US007189400B2

(12) United States Patent
Carter et al.

(10) Patent No.: US 7,189,400 B2
(45) Date of Patent: Mar. 13, 2007

(54) METHODS OF TREATMENT WITH ANTAGONISTS OF MU-1

(75) Inventors: Laura Carter, Medford, MA (US);
Matthew J. Whitters, Hudson, MA (US); Mary Collins, Natick, MA (US);
Deborah A. Young, Melrose, MA (US);
Debra D. Donaldson, Medford, MA (US); Lesile D. Lowe, Sudbury, MA (US); Michelle Unger, Brighton, MA (US)

(73) Assignee: Genetics Institute, LLC, Cambridge, MA (US)

( * ) Notice: Subject to any disclaimer, the term of this patent is extended or adjusted under 35 U.S.C. 154(b) by 0 days.

(21) Appl. No.: 09/972,218

(22) Filed: Oct. 4, 2001

(65) Prior Publication Data

US 2003/0049798 A1 Mar. 13, 2003

Related U.S. Application Data

(63) Continuation-in-part of application No. 09/569,384, filed on May 11, 2000, and a continuation-in-part of application No. 09/950,766, filed on Apr. 28, 2000, now abandoned, and a continuation-in-part of application No. 09/040,005, filed on Mar. 17, 1998, now Pat. No. 6,057,128.

(51) Int. Cl.
*A61K 39/00* (2006.01)
*A61K 39/315* (2006.01)
*A61K 38/17* (2006.01)

(52) U.S. Cl. .................. 424/185.1; 424/143.1; 424/141.1; 424/192.1; 514/2; 514/12; 530/350; 530/388.22; 536/23.5; 536/23.4

(58) Field of Classification Search ................ 530/350, 530/388.22, 388.1; 424/192.1, 130.1; 514/12
See application file for complete search history.

(56) References Cited

U.S. PATENT DOCUMENTS

| 5,011,912 | A | 4/1991 | Hopp et al. | 530/387 |
|---|---|---|---|---|
| 5,098,833 | A | 3/1992 | Lasky et al. | 435/69.1 |
| 5,116,964 | A | 5/1992 | Capon et al. | 536/27 |
| 5,155,027 | A | 10/1992 | Sledziewski et al. | 435/69.7 |
| 5,216,131 | A | 6/1993 | Lasky et al. | 530/350 |
| 5,225,538 | A | 7/1993 | Capon et al. | |
| 5,428,130 | A | 6/1995 | Capon et al. | |
| 5,447,851 | A | 9/1995 | Beutler et al. | |
| 5,455,165 | A | 10/1995 | Capon et al. | |
| 5,514,582 | A | 5/1996 | Capon et al. | |
| 5,567,584 | A | 10/1996 | Sledziewski et al. | 435/6 |
| 5,714,147 | A | 2/1998 | Capon et al. | |
| 5,750,375 | A | 5/1998 | Sledziewski et al. | 435/69.7 |
| 5,840,844 | A | 11/1998 | Lasky et al. | 530/350 |
| 5,843,725 | A | 12/1998 | Sledziewski et al. | 435/69.7 |
| 6,018,026 | A | 1/2000 | Sledziewski et al. | 530/350 |
| 6,057,128 | A | 5/2000 | Donaldson et al. | |
| 6,136,310 | A | 10/2000 | Hanna et al. | |
| 6,291,212 | B1 | 9/2001 | Sledziewski et al. | 435/69.1 |
| 6,291,646 | B1 | 9/2001 | Sledziewski et al. | 530/350 |
| 6,300,099 | B1 | 10/2001 | Sledziewski et al. | 435/69.1 |
| 6,307,024 | B1* | 10/2001 | Novak et al. | 530/351 |
| 6,323,323 | B1 | 11/2001 | Sledziewski et al. | 530/387.3 |
| 6,406,697 | B1 | 6/2002 | Capon et al. | 424/178.1 |
| 6,576,744 | B1 | 6/2003 | Presnell et al. | 530/351 |
| 2002/0090680 | A1 | 7/2002 | Hodge | 435/69.1 |
| 2002/0128446 | A1 | 9/2002 | Novak et al. | 530/351 |
| 2002/0137677 | A1* | 9/2002 | Sprecher et al. | 514/12 |

FOREIGN PATENT DOCUMENTS

| EP | 0 812 913 | | 12/1997 |
|---|---|---|---|
| EP | 1 088 831 | A1 | 4/2001 |
| WO | WO 97/20926 | | 6/1997 |
| WO | WO 97/31946 | | 9/1997 |
| WO | WO 97/33913 | | 9/1997 |
| WO | WO 97/47741 | | 12/1997 |
| WO | WO 97/47742 | | 12/1997 |
| WO | WO 98/10638 | | 3/1998 |
| WO | WO 98/11225 | | 3/1998 |
| WO | WO 98/31811 | | 7/1998 |
| WO | WO 99/47675 | | 9/1999 |
| WO | WO 00/08152 | | 2/2000 |
| WO | WO 00/17235 | | 3/2000 |
| WO | WO 00/53761 | | 9/2000 |
| WO | WO 01/46261 | | 6/2001 |

OTHER PUBLICATIONS

GenBank Database Accession No. M26062 (Jan. 6, 1995).
Parrish-Novak, et al. (2000). "Interleukin 21 and its receptor are involved in NK cell expansion and regulation of lymphocyte function" *Nature* 408: 57-63.
Yan, et al. (2000). "Two-Amino Acid Molecular Switch in an Epithelial Morphogen that Regulates Binding to Two Distinct Receptors" *Science* 290: 523-527.
Ozaki, et al. (2000). "Cloning of a type I cytokine receptor most related to the IL-2 receptor β chain" *Proc. Natl. Acad. Sci. USA* 97(21): 11439-11444.
EMBL Database Accession No. AC002303 (Jun. 26, 1997).
Bazan (1990). "Structural design and molecular evolution of a cytokine receptor superfamily" *Proc. Natl. Acad. Sci. USA* 87:6934-6938.
Dusanter-Fourt, et al. (1994). "Trasduction du signal par les recepteurs de cytokines" *Medecine/Sciences* 10: 825-835. English Abstract.
Hatakeyama, et al. (1989). "Interleukin-2 Receptor beta Chain Gene: Generation of Three Receptor Forms by Cloned Human alpha and beta Chain cDNA's" *Science* 244: 551-556.

(Continued)

*Primary Examiner*—Eileen B. O'Hara
(74) *Attorney, Agent, or Firm*—Fitzpatrick, Cella, Harper & Scinto

(57) ABSTRACT

Provided is a method of suppressing an immune response in a subject by administering an antagonist of a MU-1 hematopoietin receptor superfamily chain protein.

38 Claims, 10 Drawing Sheets

OTHER PUBLICATIONS

D'Andrea, et al. (1989). "Expression Cloning of the Murine Erythropoietin Receptor" *Cell* 57: 277-285.

O'Dowd, et al. (1997). "Cloning and chromosomal mapping of four putative novel human G-protein-coupled receptor genes" *Gene* 187(1): 75-81.

International Search Report for PCT/US 99/05854. Mailed on Aug. 17, 1999.

Biró, et al., "The Effect of WSEWS Pentapeptide and WSEWS-Specific Monoclonal Antibodies on Constitutive and IL-6 Induced Acute-Phase Protein Production by a Human Hepatoma Cell Line, HEPG-2", *Immunology Letters*, 46:183-187 (1995).

Caput, et al., "Cloning and Characterization of a Specific Interleukin (IL)-13 Binding Protein Structurally Related to the IL-5 Receptor α Chain," *Journal of Biological Chemistry*, 271(28):16921-16926 (1996).

Database EMBL, ID HS795114 Accession No. R52795, May 25, 1995.

Database EMBL, Accession No. AF279436, Jul. 18, 2000.

Database EMBL, Accession No. AB049137, Sep. 23, 2000.

Debinski, et al., "A Novel Chimeric Protein Composed of Interleukin 13 and Pseudomonas Exotoxin is Highly Cytotoxic to Human Carcinoma Cells Expressing Receptors for Interleukin 13 and Interleukin 4," *Journal of Biological Chemistry*, 270(28):16775-16780 (1995).

Lai, et al., "STAT3 and STAT5B Are Targets of Two Different Signal Pathways Activated by Hematopoietin Receptors and Control Transcription via Separate Cytokine Response Elements," *Journal of Biological Chemistry* 270(40):23254-23257 (1995).

Page, et al., "An Antiproliferative Bioassay for Interleukin-4," *Journal of Immunological Methods*, 189:129-135, (1996).

Vita, et al., "Characterization and Comparison of the Interleukin 13 Receptor with the Interleukin 4 Receptor on Several Cell Types," *Journal of Biological Chemistry*, 270(8):3512-3517 (1995).

Zhang, et al., "Identification, Purification, and Characterization of a Soluble Interleukin (IL)-13-Binding Protein," *Journal of Biological Chemistry*, 272(14):9474-9480 (1997).

* cited by examiner

FIG.1A

```
   1  GTCGACGCGG CGGTACCAGC TGTCTGCCCA CTTCTCCTGT GGTGTGCCTC
  51  ACGGTCACTT GCTTGTCTGA CCGCAAGTCT GCCCATCCCT GGGGCAGCCA
 101  ACTGGCCTCA GCCCGTGCCC CAGGCGTGCC CTGTCTCTGT CTGGCTGCCC
 151  CAGCCCTACT GTCTTCCTCT GTGTAGGCTC TGCCCAGATG CCCGGCTGGT
 201  CCTCAGCCTC AGGACTATCT CAGCAGTGAC TCCCCTGATT CTGGACTTGC
 251  ACCTGACTGA ACTCCTGCCC ACCTCAAACC TTCACCTCCC ACCACCACCA
 301  CTCCGAGTCC CGCTGTGACT CCCACGCCCA GGAGACCACC CAAGTGCCCC
 351  AGCCTAAAGA ATGGCTTTCT GAGAAAGACC CTGAAGGAGT AGGTCTGGGA
 401  CACAGCATGC CCGGGGCCC AGTGGCTGCC TTACTCCTGC TGATTCTCCA
 451  TGGAGCTTGG AGCTGCCTGG ACCTCACTTG CTACACTGAC TACCTCTGGA
 501  CCATCACCTG TGTCCTGGAG ACACGGAGCC CCAACCCCAG CATACTCAGT
 551  CTCACCTGGC AAGATGAATA TGAGGAACTT CAGGACCAAG AGACCTTCTG
 601  CAGCCTACAC AGGTCTGGCC ACAACACCAC ACATATATGG TACACGTGCC
 651  ATATGCGCTT GTCTCAATTC CTGTCCGATG AAGTTTTCAT TGTCAATGTG
 701  ACGGACCAGT CTGGCAACAA CTCCCAAGAG TGTGGCAGCT TTGTCCTGGC
 751  TGAGAGCATC AAACCAGCTC CCCCCTTGAA CGTGACTGTG GCCTTCTCAG
 801  GACGCTATGA TATCTCCTGG GACTCAGCTT ATGACGAACC CTCCAACTAC
 851  GTGCTGAGGG GCAAGCTACA ATATGAGCTG CAGTATCGGA ACCTCAGAGA
 901  CCCCTATGCT GTGAGGCCGG TGACCAAGCT GATCTCAGTG GACTCAAGAA
 951  ACGTCTCTCT TCTCCCTGAA GAGTTCCACA AAGATTCTAG CTACCAGCTG
1001  CAGGTGCGGG CAGCGCCTCA GCCAGGCACT TCATTCAGGG GGACCTGGAG
1051  TGAGTGGAGT GACCCCGTCA TCTTTCAGAC CCAGGCTGGG GAGCCCGAGG
1101  CAGGCTGGGA CCCTCACATG CTGCTGCTCC TGGCTGTCTT GATCATTGTC
1151  CTGGTTTTCA TGGGTCTGAA GATCCACCTG CCTTGGAGGC TATGGAAAAA
1201  GATATGGGCA CCAGTGCCCA CCCCTGAGAG TTTCTTCCAG CCCCTGTACA
1251  GGGAGCACAG CGGGAACTTC AAGAAATGGG TTAATACCCC TTTCACGGCC
1301  TCCAGCATAG AGTTGGTGCC ACAGAGTTCC ACAACAACAT CAGCCTTACA
1351  TCTGTCATTG TATCCAGCCA AGGAGAAGAA GTTCCCGGGG CTGCCGGGTC
1401  TGGAAGAGCA ACTGGAGTGT GATGGAATGT CTGAGCCTGG TCACTGGTGC
```

FIG. 1ß

```
1451  ATAATCCCCT TGGCAGCTGG CCAAGCGGTC TCAGCCTACA GTGAGGAGAG
1501  AGACCGGCCA TATGGTCTGG TGTCCATTGA CACAGTGACT GTGGGAGATG
1551  CAGAGGGCCT GTGTGTCTGG CCCTGTAGCT GTGAGGATGA TGGCTATCCA
1601  GCCATGAACC TGGATGCTGG CCGAGAGTCT GGCCCTAATT CAGAGGATCT
1651  GCTCTTGGTC ACAGACCCTG CTTTTCTGTC TTGCGGCTGT GTCTCAGGTA
1701  GTGGTCTCAG GCTTGGAGGC TCCCCAGGCA GCCTACTGGA CAGGTTGAGG
1751  CTGTCATTTG CAAAGGAAGG GGACTGGACA GCAGACCCAA CCTGGAGAAC
1801  TGGGTCCCCA GGAGGGGGCT CTGAGAGTGA AGCAGGTTCC CCCCCTGGTC
1851  TGGACATGGA CACATTTGAC AGTGGCTTTG CAGGTTCAGA CTGTGGCAGC
1901  CCCGTGGAGA CTGATGAAGG ACCCCCTCGA AGCTATCTCC GCCAGTGGGT
1951  GGTCAGGACC CCTCCACCTG TGGACAGTGG AGCCCAGAGC AGCTAGCATA
2001  TAATAACCAG CTATAGTGAG AAGAGGCCTC TGAGCCTGGC ATTTACAGTG
2051  TGAACATGTA GGGGTGTGTG TGTGTGTGTG TGTGTGTGTG TGTGTGTGTG
2101  TGTGTGTGTG TGTGTGTGTG TGTCTTGGGT TGTGTGTTAG CACATCCATG
2151  TTGGGATTTG GTCTGTTGCT ATGTATTGTA ATGCTAAATT CTCTACCCAA
2201  AGTTCTAGGC CTACGAGTGA ATTCTCATGT TTACAAACTT GCTGTGTAAA
2251  CCTTGTTCCT TAATTTAATA CCATTGGTTA AATAAAATTG GCTGCAACCA
2301  ATTACTGGAG GGATTAGAGG TAGGGGGCTT TTGAGTTACC TGTTTGGAGA
2351  TGGAGAAGGA GAGAGGAGAG ACCAAGAGGA GAAGGAGGAA GGAGAGGAGA
2401  GGAGAGGAGA GGAGAGGAGA GGAGAGGAGA GGAGAGGAGA GGAGAGGAGA
2451  GGCTGCCGTG AGGGGAGAGG GACCATGAGC CTGTGGCCAG GAGAAACAGC
2501  AAGTATCTGG GGTACACTGG TGAGGAGGTG GCCAGGCCAG CAGTTAGAAG
2551  AGTAGATTAG GGGTGACCTC CAGTATTTGT CAAAGCCAAT TAAAATAACA
2601  AAAAAAAAAA AAAAGCGGCC GCTCTAGA
```

FIG.2

```
  1  MPRGPVAALL  LLILHGAWSC  LDLTCYTDYL  WTITCVLETR  SPNPSILSLT
 51  WQDEYEELQD  QETFCSLHRS  GHNTTHIWYT  CHMRLSQFLS  DEVFIVNVTD
101  QSGNNSQECG  SFVLAESIKP  APPLNVTVAF  SGRYDISWDS  AYDEPSNYVL
151  RGKLQYELQY  RNLRDPYAVR  PVTKLISVDS  RNVSLLPEEF  HKDSSYQLQV
201  RAAPQPGTSF  RGTWSEWSDP  VIFQTQAGEP  EAGWDPHMLL  LLAVLIIVLV
251  FMGLKIHLPW  RLWKKIWAPV  PTPESFFQPL  YREHSGNFKK  WVNTPFTASS
301  IELVPQSSTT  TSALHLSLYP  AKEKKFPGLP  GLEEQLECDG  MSEPGHWCII
351  PLAAGQAVSA  YSEERDRPYG  LVSIDTVTVG  DAEGLCVWPC  SCEDDGYPAM
401  NLDAGRESGP  NSEDLLLVTD  PAFLSCGCVS  GSGLRLGGSP  GSLLDRLRLS
451  FAKEGDWTAD  PTWRTGSPGG  GSESEAGSPP  GLDMDTFDSG  FAGSDCGSPV
501  ETDEGPPRSY  LRQWVVRTPP  PVDSGAQSS
```

FIG. 3A

```
huMU-1   ................NNGTCGACTGGAGGCCCAGCTGCCCGTCATCA  32
              ::||   |      |||||||  |||||||  |
murMU-1  CAGCCCTACTGTCTTCCTCTGTGTAGGCTCTGCCCAGATGCCCGGC....  196 huMU-1   GAGTGACAGGTCTTATGACAGCCTGATTGGTGACTCGGGCTGGGTGTGGA  82
          ||    |  || | |||   || |   |||||||   |||  |  ||||
murMU-1  TGGTCCTCAGCCTCAGGACTATCTCAGCAGTGACTC.CCCTGATTCTGGA  245 huMU-1   TTCTCACCCCAGGCCTCTGCCTGCTTTCTCAGACCCTCATCT...GTCAC  129
         |  ||||  |       || |  |     |||| ||| ||| ||   |||
murMU-1  CTTGCACCTGACTGAACTCCTGCCCACCTCAAACCTTCACCTCCCACCAC  295 huMU-1   CCCCACGCTGAACCCAGCTG......CCACCCCCAGAAGCCCATCAGACT  173
         |  |||| |  ||  ||||       ||||  |||||  || |||  | |
murMU-1  CACCACTCCGAGTCCCGCTGTGACTCCCACGCCCAGGAGACCACCCAAGT  345 huMU-1   GCCCCAGCACACGGAATGGATTTCTGAGAAAGAAGCCGAAACAGAAGGC   223
         | ||||||| |   ||||||  ||||||||||| |   |||   || |||
murMU-1  G.CCCCAGCCTAAAGAATGGCTTTCTGAGAAAGACCCTGAAGGAGTAGGT  394 huMU-1   CCGTGGGAGTCAGCATGCCGCGTGGCTGGGCCGCCCCCTTGCTCCTGCTG  273
         |   |||||  ||||||||| ||   ||   |     | ||  ||||||||||
murMU-1  C..TGGGACACAGCATGCCCCGGGGCCCAGTGGCTGCCTTACTCCTGCTG  442 huMU-1   CTGCTCCAGGGAGGCTGGGGCTGCCCCGACCTCGTCTGCTACACCGATTA  323
         |  |||||| ||||    ||| ||||||||  ||||||       || ||
murMU-1  ATTCTCCATGGAGCTTGGAGCTGCCTGGACCTCACTTGCTACACTGACTA  492 huMU-1   CCTCCAGACGGTCATCTGCATCCTGGAAATGTGGAACCTCCACCCCAGCA  373
         ||||  |||   ||| |||  ||||||||| |    ||| ||  ||||||||||
murMU-1  CCTCTGGACCATCACCTGTGTCCTGGAGACACGGAGCCCCAACCCCAGCA  542 huMU-1   CGCTCACCCTTACCTGGCAAGACCAGTATGAAGAGCTGAAGGACGAGGCC  423
         ||||  || |||||||||||  |||||| || || ||||| | |
murMU-1  TACTCAGTCTCACCTGGCAAGATGAATATGAGGAACTTCAGGACCAAGAG  592 huMU-1   ACCTCCTGCAGCCTCCACAGGTCGGCCCACAATGCCACGCATGCCACCTA  473
         ||||  |||||||||| ||||||||  |  | ||||| ||||  |||   ||
murMU-1  ACCTTCTGCAGCCTACACAGGTCTGGCCACAACACCACACATATATGGTA  642 huMU-1   CACCTGCCACATGGATGTATTCCACTTCATGGCCGACGACATTTTCAGTG  523
         |||  ||||| |||     | |   || || || || ||||| ||||||  ||
murMU-1  CACGTGCCATATGCGCTTGTCTCAATTCCTGTCCGATGAAGTTTTCATTG  692 huMU-1   TCAACATCACAGACCAGTCTGGCAACTACTCCCAGGAGTGTGGCAGCTTT  573
         ||||  |  ||  |||||||||||||||||||||| |||||||  |||||||||||||
murMU-1  TCAATGTGACGGACCAGTCTGGCAACAACTCCCAAGAGTGTGGCAGCTTT  742 huMU-1   CTCCTGGCTGAGAGCATCAAGCCGGCTCCCCCTTTCAACGTGACTGTGAC  623
         |||||||||||||||||||||||  ||  |||||||||| ||||||||||||||  |
murMU-1  GTCCTGGCTGAGAGCATCAAACCAGCTCCCCCCTTGAACGTGACTGTGGC  792 huMU-1   CTTCTCAGGACAGTATAATATCTCCTGGCGCTCAGATTACGAAGACCCTG  673
         ||||||||||||   ||| |||||||||||  |||||   || || ||  ||
murMU-1  CTTCTCAGGACGCTATGATATCTCCTGGGACTCAGCTTATGACGAACCCT  842 huMU-1   CCTTCTACATGCTGAAGGGCAAGCTTCAGTATGAGCTGCAGTACAGGAAC  723
         ||  ||||  ||||||  ||||||||||||| ||  ||||||||||||||||||||  |||||
murMU-1  CCAACTACGTGCTGAGGGGCAAGCTACAATATGAGCTGCAGTATCGGAAC  892 huMU-1   CGGGGAGACCCCTGGGCTGTGAGTCCGAGGAGAAAGCTGATCTCAGTGGA  773
         |     |||||||||  ||||||||| |||   ||   ||||||||||||||||||||||
murMU-1  CTCAGAGACCCCTATGCTGTGAGGCCGGTGACCAAGCTGATCTCAGTGGA  942 huMU-1   CTCAAGAAGTGTCTCCCTCCTCCCCCTGGAGTTCCGCAAAGACTCGAGCT  823
```

FIG.3$

```
             IIIIIIII  IIIII  II IIIII     IIIIIIII IIIIII II IIII
murMU-1   CTCAAGAAACGTCTCTCTTCTCCCTGAAGAGTTCCACAAAGATTCTAGCT 992 huMU-1    ATGAGCTGCAGGTGCGGGCAGGGCCCATGCCTGGCTCCTCCTACCAGGGG 873
           I IIIIIIIIIIIIIIIIIII III   III III I II I I  IIII
murMU-1   ACCAGCTGCAGGTGCGGGCAGCGCCTCAGCCAGGCACTTCATTCAGGGGG 1042 huMU-1    ACCTGGAGTGAATGGAGTGACCCGGTCATCTTTCAGACCCAGTCAGAGGA 923
          IIIIIIIIIII IIIIIIIIIIII IIIIIIIIIIIIIIIIII I I III
murMU-1   ACCTGGAGTGAGTGGAGTGACCCCGTCATCTTTCAGACCCAGGCTGGGGA 1092 huMU-1    GTTAAAGGAAGGCTGGAACCCTCACCTGCTGCTTCTCCTCCTGCTTGTCA 973
           I   III IIIIIIII IIIIIIII IIIII   II IIIIII  IIII
murMU-1   GCCCGAGGCAGGCTGGGACCCTCACATGCTG...CTGCTCCTGGCTGTCT 1139 huMU-1    TAGTCTTCATTCCTGCCTTCTGGAGCCTGAAGACCCATCCATTGTGGAGG 1023
           I  II I  I I  I  III  I I IIIIIIII III I    IIIIII
murMU-1   TGATCATTGTCCTGGTTTTCATGGGTCTGAAGATCCACCTGCCTTGGAGG 1189 huMU-1    CTATGGAAGAAGATATGGG...CCGTCCCCAGCCCTGAGCGGTTCTTCAT 1070
          IIIIIIII IIIIIIIIII   I II IIII IIIIIII I IIIIII
murMU-1   CTATGGAAAAAGATATGGGCACCAGTGCCCACCCCTGAGAGTTTCTTCCA 1239 huMU-1    GCCCCTGTACAAGGGCTGCAGCGGAGACTTCAAGAAATGGGTGGGTGCAC 1120
          IIIIIIIIIII II   IIIIII  IIIIIIIIIIIIIIII   I I I
murMU-1   GCCCCTGTACAGGGAGCACAGCGGGAACTTCAAGAAATGGGTTAATACCC 1289 huMU-1    CCTTCACTGGCTCCAGCCTGGAGCTGGGACCCTGGAGCCCAGAGGTGCCC 1170
          I IIIIII I IIIIIII I III III  II   III  I         I
murMU-1   CTTTCACGGCCTCCAGCATAGAGTTGGTGCCACAGAGTTCCACAACAACA 1339 huMU-1    TCCACCCTGGAGGTGTACAGCTGCCACCCACCACGGAGCCCGGCCAAGAG 1220
          II  II  I  I III              II  I  II IIIIII
murMU-1   TCAGCCTTACATCTGT...............CATTGTATCCAGCCAAGGA 1374 huMU-1    GCTGCAGCTCACGGAGCTACAAGAACCAGCAGAGCTGGTGGAGTCTGACG 1270
          I  I II II  III III  I   I  I IIIII   IIIIII III I
murMU-1   GAAGAAGTTCCCGGGGCTGCCGGGTCTGGAAGAGCAACTGGAGTGTGATG 1424 huMU-1    GTGTGCCCAAGCCCAGCTTCTGG.........CCGACAGCCCAGAACTCG 1311
          I  II I IIII  I   IIII         II   II         I
murMU-1   GAATGTCTGAGCCTGGTCACTGGTGCATAATCCCCTTGGCAGCTGGCCAA 1474 huMU-1    GGGGGCTCAGCTTACAGTGAGGAGAGGGATCGGCCATACGGCCTGGTGTC 1361
          I II IIIIII IIIIIIIIIIIIII II IIIIIIII II IIIIIIII
murMU-1   GCGGTCTCAGCCTACAGTGAGGAGAGAGACCGGCCATATGGTCTGGTGTC 1524 huMU-1    CATTGACACAGTGACTGTGCTAGATGCAGAGGGGCCATGCACCTGGCCCT 1411
          IIIIIIIIIIIIIIIIIII IIIIIIIIIII I II   IIIIIIIII
murMU-1   CATTGACACAGTGACTGTGGGAGATGCAGAGGGCCTGTGTGTCTGGCCCT 1574 huMU-1    GCAGCTGTGAGGATGACGGCTACCCAGCCCTGGACCTGGATGCTGGCCTG 1461
          I IIIIIIIIIIIIII IIIII IIIIII II IIIIIIIIIIIIIIII
murMU-1   GTAGCTGTGAGGATGATGGCTATCCAGCCATGAACCTGGATGCTGGCCGA 1624 huMU-1    GAGCCCAGCCCAGGCCTAGAGGACCCACTCTTGGATGCAGGGACCACAGT 1511
          III I  IIII    IIIIIII I IIIIIII III  I I  I I
murMU-1   GAGTCTGGCCCTAATTCAGAGGATCTGCTCTTGGTCACAGACCCTGCTTT 1674 huMU-1    CCTGTCCTGTGGCTGTGTCTCAGCTGGCAGCCCTGGGCTAGGAGGGCCCC 1561
          IIIII II IIIIIIIIIIIIII I I  I I    IIII IIIII  III
murMU-1   TCTGTCTTGCGGCTGTGTCTCAGGTAGTGGTCTCAGGCTTGGAGGCTCCC 1724 huMU-1    TGGAAGCCTCCTGGACAGACTAAAGCCACCCCTTGCAGATGGGGAGGAC 1611
           II IIIII IIIIIIII  I I II   I  IIIIII I I  I IIII
murMU-1   CAGGCAGCCTACTGGACAGGTTGAGGCTGTCATTTGCAAAGGAAGGGGAC 1774 huMU-1    TGGGCTGGGGGACTGCCCTGGGGTGGCCGGTCACCTGGAGGGGTCTCAGA 1661
```

FIG.3c

```
              ||| | | |   ||||| |      |||| || ||||||| ||| ||
murMU-1    TGGACAGCAGACCCAACCTGGAGAACTGGGTCCCCAGGAGGGGGCTCTGA  1824
                                  .                     .
huMU-1     GAGTGAGGCGGGCTCACCCCTGGCCGGCCTGGATATGGACACGTTTGACA  1711
           |||||| || || || ||||   | || ||||| ||||||||| |||||||
murMU-1    GAGTGAAGCAGGTTCCCCCC...CTGGTCTGGACATGGACACATTTGACA  1871
                                  .                     .
huMU-1     GTGGCTTTGTGGGCTCTGACTGCAGCAGCCCTGTGGAGTGTGACTTCACC  1761
           |||||||||  || || |||||  |||||||| ||||||  |
murMU-1    GTGGCTTTGCAGGTTCAGACTGTGGCAGCCCGTGGAGACT.........  1912
                                  .                     .
huMU-1     AGCCCCGGGGACGAAGGACCCCCCCGGAGCTACCTCCGCCAGTGGGTGGT  1811
                || ||||||||||||| || ||||||  ||||||||||||||||||||
murMU-1    .........GATGAAGGACCCCCTCGAAGCTATCTCCGCCAGTGGGTGGT  1953
                                  .                     .
huMU-1     CATTCCTCCGCCACTTTCGAGCCCTGGACCCCAGGCCAGCTAATGAGGCT  1861
           ||   | || |||| |  |   |   ||||  |||||   ||||||
murMU-1    CAGGACCCCTCCACCTGTGGACAGTGGAGCCCAGAGCAGCTA........  1995
                                  .                     .
huMU-1     GACTGGATGTCCAGAGCTGGCCAGGCCACTGGGCCCTGAGCCAGAGACAA  1911
             |    |    ||||     |   |  ||  |  ||||||||
murMU-1    .GCATATAATAACCAGCTATAGTGAGAAGAGGCCTCTGAGCC........  2036
                                  .                     .
huMU-1     TGGGCCTTTGAGCCTGATGTTTACAGTGTCTGTGTGTGTGTGTGCATATG  2011
           |||   ||  ||  |||   |    | || |||||||||||||  | ||
murMU-1    TGGCATTTACAGTGTGAACATGTAGGGGTGTGTGTGTGTGTGTGTGTGTG  2086
                                  .                     .
huMU-1     TGTGTGTGTGCATATGCATGTGTGTGTGTGTGTGTGTCTTACTGGACTCA  2061
           |||||||||  | ||   ||||||||||||||||||||||   |    |
murMU-1    TGTGTGTGTGTGTGTGTGTGTGTGTGTGTGTGTGTCTT.GGGTTGTGT   2135
                                  .                     .
huMU-1     CGGAGCTCACCCATGTGCACAAGTGTGCACAGTAAACGTGTTTGTGGTCA  2111
             ||| ||  ||||||    |  ||           || |||  |    |
murMU-1    GTTAGCACATCCATGTTGGGATTTG..............GTCTGTTGCTA  2171
                                  .                     .
huMU-1     ACAGATGACAACAGCCGTCCTCCCTCCTAGGGTCTTGTGTTGCAAGTTGG  2161
              || |       |   |||   || | | ||| |   | | |||
murMU-1    TGTATTGTAATGCTAAATTCTCTACCCAAAGTTCTAGGCCTACGAGTGAA  2221
                                  .                     .
huMU-1     TCCACAGCATCTCCGGGGCTTTGTGGGATCAGGGCATTGCCTGTGACTGA  2211
           | | ||    |  |  |     ||||  | |   | |||        | |
murMU-1    TTCTCATGTTTACAAACTTGCTGTGTAAACCTTG...TTCCTTAATTTAA  2268
                                  .                     .
huMU-1     GGCGGAGCCCAGCCCTCCAGCGTCTGCCTCCAGGAGCTGCAAGAAGTCCA  2261
             |              |   | |||| |||    ||| | | |   |
murMU-1    TACCATTGGTTAAATAAAATTGGCTGCAACCAATTACTGGAGGGATTAGA  2318
                                  .                     .
huMU-1     TATTG.....TTCCTTATCACCTGCCAACAGGAAGCGAAAGGGGATGGAG  2306
             | |     ||    | ||||||   ||  | ||| ||    ||||
murMU-1    GGTAGGGGGCTTTTGAGTTACCTGTTTGGAGATGGAGAAGGAGAGAGGAG  2368
                                  .                     .
huMU-1     TGAGCCCATGGTGACCTCGGGAATGGCAATTTTTTGGGCGGCCCCTGGAC  2356
           ||   ||  ||  || ||   | |  | |    | |     || ||   |
murMU-1    AGACCAAGAGGAGAAGGAGGAAGGAGAGGAGAGGAGAGGAGAGGAGAGGA  2418
                                  .                     .
huMU-1     GAAGGTCTGAATCCCGACTCTGATACCTTCTGGCTGTGCTACCTGAGCCA  2406
           || |   ||    ||    ||    ||         | |||    | |
murMU-1    GAGGAGAGGAGAGGAGA.GGAGAGGAGAGGAGAGGCTGCCGTGAGGGGAG  2467
                                  .                     .
huMU-1     AGTCGCCTCCCCTCTCTGGGCTAGAGTTTCCTTATCCAGACAGTGGGGAA  2456
           ||   ||       || ||| |  ||| |   |                ||
murMU-1    AGGGACCATGAGCCTGTGGCCAGGAGAAACAGCA............AGTA  2505
                                  .                     .
huMU-1     GGCATGACACACCTGGGGGAAATTGGCGATGTCACCCGTGTACGGTACGC  2506
            |  ||||  | | ||  ||||| | || ||  ||  | |   |    |
murMU-1    TCTGGGGTACACTGGTGAGGAGGTGGCCAGGCCAGC...AGTTAGAAGAGT  2553
                                  .                     .
huMU-1     AGCCCAGAGCAGACCCTCAATAAACGTCAGCTTCCTTCAAAAAAAAAAAA  2556
```

FIG.3l

```
              ||    || |  ||||  || ||   ||||     |  | ||||  || ||||
murMU-1   AGATTAGGGGTGACCTCCAGTATTTGTCAAAGCCAATTAAAATAACAAAA  2603 huMU-1    AAAAATCTAGA..............  2567
              |||||    | |
murMU-1   AAAAAAAAAAAGCGGCCGCTCTAGA  2628
```

FIG.4

```
Human MU-1    MPRGWAAPLLLLLLQGGWGCPDLVCYTDYLQTVICILEMWNLHPSTLTLT 50
              ||||  |  ||||:|  |  |  |  ||  ||||||  |:  |:||  .  .||  |.||
MurineMU-1    MPRGPVAALLLLILHGAWSCLDLTCYTDYLWTITCVLETRSPNPSILSLT 50

Human MU-1    WQDQYEELKDEATSCSLHRSAHNATHATYTCHMDVFHFMADDIFSVNITD 100
              |||:||||.|:  |  ||||||  ||  ||  |||||  .    |:.|::|  ||:||
MurineMU-1    WQDEYEELQDQETFCSLHRSGHNTTHIWYTCHMRLSQFLSDEVFIVNVTD 100

Human MU-1    QSGNYSQECGSFLLAESIKPAPPFNVTVTFSGQYNISWRSDYEDPAFYML 150
              ||||  |||||||.-|||||||||||  ||||  |||.|-|.|||  |  |::|.  |.|
MurineMU-1    QSGNNSQECGSFVLAESIKPAPPLNVTVAFSGRYDISWDSAYDEPSNYVL 150

Human MU-1    KGKLQYELQYRNRGDPWAVSPRRKLISVDSRSVSLLPLEFRKDSSYELQV 200
              :||||||||||||    ||:||  |  ||||||||.|||||  ||  |||||:|||
MurineMU-1    RGKLQYELQYRNLRDPYAVRPVTKLISVDSRNVSLLPEEFHKDSSYQLQV 200

Human MU-1    RAGPMPGSSYQGTWSEWSDPVIFQTQSEELKEGWNPHLLLLLLLVIVFIP 250
              ||  |  ||.|:.||||||||||||||||.  |  -  ||.||:||||  ..|:  :
MurineMU-1    RAAPQPGTSFRGTWSEWSDPVIFQTQAGEPEAGWDPHMLLLLAVLIIVL. 249

Human MU-1    AFWSLKTHPLWRLWKKIWA.VPSPERFFMPLYKGCSGDFKKWVGAPFTGS 299
              |    ||  |    |||||||||  ||.||  ||  ||||:    ||.|||||  |||  |
MurineMU-1    VFMGLKIHLPWRLWKKIWAPVPTPESFFQPLYREHSGNFKKWVNTPFTAS 299

Human MU-1    SLELGPWSPEVPSTLEVYSCHPPRSPAKRLQLTELQEPAELVESDGVPKP 349
              |:||  |  |    ||  |        |   |||  .    |    |  .|  ||.  .|
MurineMU-1    SIELVPQSSTTTSAL.....HLSLYPAKEKKFPGLPGLEEQLECDGMSEP 344

Human MU-1    SFW...PTAQNSGGSAYSEERDRPYGLVSIDTVTVLDAEGPCTWPCSCED 396
              |    ||    |||||||||||||||||||||||  ||||  |  |||||||
MurineMU-1    GHWCIIPLAAGQAVSAYSEERDRPYGLVSIDTVTVGDAEGLCVWPCSCED 394

Human MU-1    DGYPALDLDAGLEPSPGLEDPLLDAGTTVLSCGCVSAGSPGLGGPLGSLL 446
              |||||:.||||  |  |  ||  ||        |||||||        |||  ||||
MurineMU-1    DGYPAMNLDAGRESGPNSEDLLLVTDPAFLSCGCVSGSGLRLGGSPGSLL 444

Human MU-1    DRLKPPLADGEDWAGGLPWGGRSPGGVSESEAGSPLAGLDMDTFDSGFVG 496
              |||:  |  ||  |    ||||  |||||||||  ||||||||||||  |
MurineMU-1    DRLRLSFAKEGDWTADPTWRTGSPGGGSESEAGSP.PGLDMDTFDSGFAG 493

Human MU-1    SDCSSPVECDFTSPGDEGPPRSYLRQWVV.IPPPLSSPGPQAS* 539
              |||  ||||    |||||||||||||  ||.  |  |  |.|
MurineMU-1    SDCGSPVET......DEGPPRSYLRQWVVRTPPPVDS.GAQSS. 529
```

FIG. 5

```
              1                                                           50
       humu  ---MPRGWAA PLLLLL..LQ GGWG...... CPDLVCYTDY LQTVICILEM
     mousemu ---MPRGPVA ALLLLI..LH GAWG...... CLDLTCYTDY LWTITCVLET
   humil2rbc MAAPALSWRL PLLILLLPLA TSWASAAVNG TSQFTCFYNS RANISCVWSQ
              51                                                         100
       humu  WN..LHPSTL TLTWQDQYEE LKDEATSCSL HRSAHNATHA TYTCHM....
     mousemu RS..PNPSIL SLTWQDEYEE LQDQETFCSL HRSGHNTTHI WYTCHM....
   humil2rbc DGALQDTSCQ VHAWPDR... .RRWNQTCEL ....LPVSQA SWACNLILGA
              101                                                        150
       humu  .DVFHFMADD IFSVNITDQS GN..YSQECG SFLLAESIKP APPFNVTVTF
     mousemu .RLSQFLSDE VFIVNVTDQS GN..NSQECG SFVLAESIKP APPLNVTVAF
   humil2rbc PDSQKLTTVD IVTLRVLCRE GVRWRVMAIQ DFKPFENLRL MAPISLQVVH
              151                                                        200
       humu  ..SGQYNISW RSDYEDPAFY MLKGKLQYEL QYRNRGDPWA VSPRRKLISV
     mousemu ..SGRYDISW DSAYDEPSNY VLRGKLQYEL QYRNLRDPYA VRPVTKLISV
   humil2rbc VETHRCNISW E..ISQASHY FER.HLEFEA RTLSPGHTWE EAP...LLTL
              201                                                        250
       humu  DSRSVSLLPL EFRKDSSYEL QVRAGPMPGS SYQGTWSEWS DPVIFQTQS.
     mousemu DSRNVSLLPE EFHKDSSYQL QVRAAPQPGT SFRGTWSEWS DPVIFQTQA.
   humil2rbc KQKQEWICLE TLTPDTQYEF QVRVKPLQGE F..TTWSPWS QPLAFRTKPA
              251                                                        300
       humu  ..EELKEGWN PHLLLLL... LLVIVFIPAF WSLKTHPLWR LWKKIWA.VP
     mousemu ..GEPEAGWD PHMLLLL... AVLIIVL.VF MGLKIHLPWR LWKKIWAPVP
   humil2rbc ALGKDTIPWL GHLLVGLSGA FGFIILVYLL INCRNTGPW. LKKVLKCNTP
              301                                                        350
       humu  SPERFFMPLY KGCSGDFKKW VGAPFTGSSL ELGPWSPEVP STLEVYSCHP
     mousemu TPESFFQPLY REHSGNFKKW VNTPFTASSI ELVPQSSTTT SAL.....HL
   humil2rbc DPSKFFSQLS SEHGGDVQKW LSSPFPSSSF SPGGLAPEIS PLEVLERDKV
              351                                                        400
       humu  PRSPAKRLQL TELQEPA..E LVESDGVPKP SFW...PTAQ NSGGSAYSEE
     mousemu SLYPAKEKKF PGLPGLE..E QLECDGMSEP GHWCIIPLAA GQAVSAYSEE
   humil2rbc TQLLLQQDKV PEPASLSSNH SLTSCFTNQG YFFFHLPDAL EIEACQVYFT
              401                                                        450
       humu  RDRPYGLVSI DTVTVLDAEG PC...TWPCS CEDDGYPALD LDAGLEPSPG
     mousemu RDRPYGLVSI DTVTVGDAEG LC...VWPCS CEDDGYPAMN LDAGRESGPN
   humil2rbc YD.PYSEEDP DEGVAGAPTG SSPQPLQPLS GEDDAYCTF. ........PS
              451                                                        500
       humu  LEDPLLDAGT TVLSCGCVSA GSPGLGGPLG SLLDRLKPPL AD..GEDWAG
     mousemu SEDLLLVTDP AFLSCGCVSG SGLRLGGSPG SLLDRLRLSF AK..EGDWTA
   humil2rbc RDDLLLFS.P SLL..GGPSP PSTAPGGS.G AGEERMPPSL QERVPRDWDP
              501                                                        550
       humu  GLPWGGRSPG GVSESEAGSP LAGLDMDTFD SGFVGSDCSS PVECDFTSPG
     mousemu DPTWRTGSPG GGSESEAGSP .PGLDMDTFD SGFAGSDCGS PVET......
   humil2rbc Q.PLGPPTPG VPDLVDFQPP P...ELVLRE AGEEVPDAG. PRE.GVSFPW
              551                                           588
       humu  DEGPPRSYLR QWVVIPPPLS SPGPQAS*~~ ~~~~~~~~
     mousemu DEGPPRSYLR QWVVRTPPPV DSGAQSS~~~ ~~~~~~~~
   humil2rbc SRPPGQGEFR ALNARLPLNT DAYLSLQELQ GQDPTHLV
```

Signaling through MU-1

SEQUENCE LISTING

<160> NUMBER OF SEQ ID NOS: 22

<210> SEQ ID NO 1
<211> LENGTH: 2665
<212> TYPE: DNA
<213> ORGANISM: Human

<400> SEQUENCE: 1

```
gtcgactgga ggcccagctg cccgtcatca gagtgacagg tcttatgaca gcctgattgg      60
tgactcgggc tgggtgtgga ttctcacccc aggcctctgc ctgctttctc agaccctcat     120
ctgtcacccc cacgctgaac ccagctgcca ccccagaag cccatcagac tgccccagc      180 acacggaatg gatttctgag aaagaagccg aaacagaagg cccgtgggag tcagcatgcc     240
gcgtggctgg gccgcccct tgctcctgct gctgctccag ggaggctggg gctgccccga     300
cctcgtctgc tacaccgatt acctccagac ggtcatctgc atcctggaaa tgtggaacct     360
ccaccccagc acgctcaccc ttacctggca agaccagtat gaagagctga aggacgaggc     420
cacctcctgc agcctccaca ggtcggccca caatgccacg catgccacct acacctgcca     480
catggatgta ttccacttca tggccgacga cattttcagt gtcaacatca cagaccagtc     540
tggcaactac tcccaggagt gtggcagctt tctcctggct gagagcatca agccggctcc     600 cccttctcaac gtgactgtga ccttctcagg acagtataat atctcctggc gctcagatta     660
cgaagaccct gccttctaca tgctgaaggg caagcttcag tatgagctgc agtacaggaa     720 ccgggagac ccctgggctg tgagtccgag gagaaagctg atctcagtgg actcaagaag     780
tgtctccctc ctccccctgg agttccgcaa agactcgagc tatgagctgc aggtgcgggc     840 agggccatg cctggctcct cctaccaggg gacctggagt gaatggagtg accggtcat      900 ctttcagacc cagtcagagg agttaaagga aggctggaac cctcacctgc tgcttctcct     960
cctgcttgtc atagtcttca ttcctgcctt ctggagcctg aagacccatc cattgtggag    1020
gctatggaag aagatatggg ccgtcccag ccctgagcgg ttcttcatgc ccctgtacaa    1080
gggctgcagc ggagacttca agaaatgggt gggtgcaccc ttcactggct ccagcctgga    1140
gctgggaccc tggagcccag aggtgccctc caccctggag gtgtacagct gccacccacc    1200
acggagcccg gccaagaggc tgcagctcac ggagctacaa gaaccagcag agctggtgga    1260
gtctgacggt gtgcccaagc ccagcttctg gccgacagcc cagaactcgg ggggctcagc    1320
ttacagtgag gagagggatc ggccatacgg cctggtgtcc attgacacag tgactgtgct    1380
agatgcagag gggccatgca cctggcctg cagctgtgag gatgacggct acccagccct    1440
ggacctggat gctggcctgg agcccagccc aggcctagag acccactct tggatgcagg    1500 gaccacagtc ctgtcctgtg gctgtgtctc agctggcagc cctgggctag agggcccct    1560 gggaagcctc ctggacagac taaagccacc ccttgcagat ggggaggact gggctggggg    1620
actgccctgg ggtggccggt cacctggagg ggtctcagag agtgaggcgg gctcacccct    1680
ggccggcctg gatatggaca cgtttgacag tggctttgtg ggctctgact gcagcagccc    1740 tgtgagtgt gacttcacca gccccgggga cgaaggaccc ccccggagct acctccgcca    1800
gtgggtggtc attcctccgc cactttcgag ccctggaccc caggccagct aatgaggctg    1860
```

```
actggatgtc cagagctggc caggccactg ggccctgagc cagagacaag gtcacctggg      1920
ctgtgatgtg aagacacctg cagcctttgg tctcctggat gggcctttga gcctgatgtt      1980
tacagtgtct gtgtgtgtgt gtgcatatgt gtgtgtgtgc atatgcatgt gtgtgtgtgt      2040
gtgtgtctta ggtgcgcagt ggcatgtcca cgtgtgtgtg tgattgcacg tgcctgtggg      2100
cctgggataa tgcccatggt actccatgca ttcacctgcc ctgtgcatgt ctggactcac      2160
ggagctcacc catgtgcaca agtgtgcaca gtaaacgtgt ttgtggtcaa cagatgacaa      2220
cagccgtcct ccctcctagg gtcttgtgtt gcaagttggt ccacagcatc tccggggctt      2280
tgtgggatca gggcattgcc tgtgactgag gcggagccca gccctccagc gtctgcctcc      2340
aggagctgca agaagtccat attgttcctt atcacctgcc aacaggaagc gaaaggggat      2400
ggagtgagcc catggtgacc tcgggaatgg caatttttg gcggcccct ggacgaaggt       2460 ctgaatcccg actctgatac cttctggctg tgctacctga gccaagtcgc ctcccctctc      2520
tgggctagag tttccttatc cagacagtgg ggaaggcatg acacacctgg gggaaattgg      2580
cgatgtcacc cgtgtacggt acgcagccca gagcagaccc tcaataaacg tcagcttcct      2640
tcaaaaaaaa aaaaaaaat ctaga                                            2665
```

<210> SEQ ID NO 2
<211> LENGTH: 538
<212> TYPE: PRT
<213> ORGANISM: Human

<400> SEQUENCE: 2

```
Met Pro Arg Gly Trp Ala Ala Pro Leu Leu Leu Leu Leu Leu Gln Gly
  1               5                  10                  15

Gly Trp Gly Cys Pro Asp Leu Val Cys Tyr Thr Asp Tyr Leu Gln Thr
             20                  25                  30

Val Ile Cys Ile Leu Glu Met Trp Asn Leu His Pro Ser Thr Leu Thr
         35                  40                  45

Leu Thr Trp Gln Asp Gln Tyr Glu Glu Leu Lys Asp Glu Ala Thr Ser
     50                  55                  60

Cys Ser Leu His Arg Ser Ala His Asn Ala Thr His Ala Thr Tyr Thr
 65                  70                  75                  80

Cys His Met Asp Val Phe His Phe Met Ala Asp Ile Phe Ser Val
                 85                  90                  95

Asn Ile Thr Asp Gln Ser Gly Asn Tyr Ser Gln Glu Cys Gly Ser Phe
            100                 105                 110

Leu Leu Ala Glu Ser Ile Lys Pro Ala Pro Pro Phe Asn Val Thr Val
        115                 120                 125

Thr Phe Ser Gly Gln Tyr Asn Ile Ser Trp Arg Ser Asp Tyr Glu Asp
    130                 135                 140

Pro Ala Phe Tyr Met Leu Lys Gly Lys Leu Gln Tyr Glu Leu Gln Tyr
145                 150                 155                 160

Arg Asn Arg Gly Asp Pro Trp Ala Val Ser Pro Arg Arg Lys Leu Ile
                165                 170                 175

Ser Val Asp Ser Arg Ser Val Ser Leu Leu Pro Leu Glu Phe Arg Lys
            180                 185                 190

Asp Ser Ser Tyr Glu Leu Gln Val Arg Ala Gly Pro Met Pro Gly Ser
        195                 200                 205

Ser Tyr Gln Gly Thr Trp Ser Glu Trp Ser Asp Pro Val Ile Phe Gln
    210                 215                 220
```

```
Thr Gln Ser Glu Glu Leu Lys Glu Gly Trp Asn Pro His Leu Leu Leu
225                 230                 235                 240

Leu Leu Leu Leu Val Ile Val Phe Ile Pro Ala Phe Trp Ser Leu Lys
                245                 250                 255

Thr His Pro Leu Trp Arg Leu Trp Lys Lys Ile Trp Ala Val Pro Ser
            260                 265                 270

Pro Glu Arg Phe Phe Met Pro Leu Tyr Lys Gly Cys Ser Gly Asp Phe
        275                 280                 285

Lys Lys Trp Val Gly Ala Pro Phe Thr Gly Ser Ser Leu Glu Leu Gly
290                 295                 300

Pro Trp Ser Pro Glu Val Pro Ser Thr Leu Glu Val Tyr Ser Cys His
305                 310                 315                 320

Pro Pro Arg Ser Pro Ala Lys Arg Leu Gln Leu Thr Glu Leu Gln Glu
                325                 330                 335

Pro Ala Glu Leu Val Glu Ser Asp Gly Val Pro Lys Pro Ser Phe Trp
            340                 345                 350

Pro Thr Ala Gln Asn Ser Gly Gly Ser Ala Tyr Ser Glu Glu Arg Asp
        355                 360                 365

Arg Pro Tyr Gly Leu Val Ser Ile Asp Thr Val Thr Val Leu Asp Ala
370                 375                 380

Glu Gly Pro Cys Thr Trp Pro Cys Ser Cys Glu Asp Asp Gly Tyr Pro
385                 390                 395                 400

Ala Leu Asp Leu Asp Ala Gly Leu Glu Pro Ser Pro Gly Leu Glu Asp
                405                 410                 415

Pro Leu Leu Asp Ala Gly Thr Thr Val Leu Ser Cys Gly Cys Val Ser
            420                 425                 430

Ala Gly Ser Pro Gly Leu Gly Gly Pro Leu Gly Ser Leu Leu Asp Arg
        435                 440                 445

Leu Lys Pro Pro Leu Ala Asp Gly Glu Asp Trp Ala Gly Gly Leu Pro
450                 455                 460

Trp Gly Gly Arg Ser Pro Gly Gly Val Ser Glu Ser Glu Ala Gly Ser
465                 470                 475                 480

Pro Leu Ala Gly Leu Asp Met Asp Thr Phe Asp Ser Gly Phe Val Gly
                485                 490                 495

Ser Asp Cys Ser Ser Pro Val Glu Cys Asp Phe Thr Ser Pro Gly Asp
            500                 505                 510

Glu Gly Pro Pro Arg Ser Tyr Leu Arg Gln Trp Val Val Ile Pro Pro
        515                 520                 525

Pro Leu Ser Ser Pro Gly Pro Gln Ala Ser
530                 535

<210> SEQ ID NO 3
<211> LENGTH: 70
<212> TYPE: PRT
<213> ORGANISM: Human

<400> SEQUENCE: 3

Leu Met Thr Asn Ala Phe Ile Ser Ile Ile Asp Asp Leu Ser Lys Tyr
1               5                   10                  15

Asp Val Gln Val Arg Ala Ala Val Ser Ser Met Cys Arg Glu Ala Gly
                20                  25                  30

Leu Trp Ser Glu Trp Ser Gln Pro Ile Tyr Val Gly Asn Asp Glu His
            35                  40                  45

Lys Pro Leu Arg Glu Trp Phe Val Ile Val Ile Met Ala Thr Ile Cys
        50                  55                  60
```

Phe Ile Leu Leu Ile Leu
 65                  70

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: PCR Primer

<400> SEQUENCE: 4
gagtccgagg agaaagctga tctca                                         25

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: PCR Primer

<400> SEQUENCE: 5
gaaagatgac cgggtcactc catt                                          24

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Labelled
      hybridization Oligonucleotide

<400> SEQUENCE: 6
actcgagcta tgagctgcag gtgcgggca                                     29

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: NN14-1b
      (MU-1) labelled hybridization Oligonucleotide

<400> SEQUENCE: 7
actcgagcta tgagctgcag gtgcgggca                                     29

<210> SEQ ID NO 8
<211> LENGTH: 5
<212> TYPE: PRT
<213> ORGANISM: Artificial Sequence
<220> FEATURE:
<221> NAME/KEY: VARIANT
<222> LOCATION: (3)
<223> OTHER INFORMATION: Wherein Xaa is any amino acid.
<220> FEATURE:
<223> OTHER INFORMATION: Description of Artificial Sequence: Motif
      characteristic of the hematopoietin receptor
      family

<400> SEQUENCE: 8

Trp Ser Xaa Trp Ser
 1               5

<210> SEQ ID NO 9
<211> LENGTH: 2628
<212> TYPE: DNA
<213> ORGANISM: Mouse

<400> SEQUENCE: 9

| | | | | | |
|---|---|---|---|---|---|
| gtcgacgcgg | cggtaccagc | tgtctgccca | cttctcctgt | ggtgtgcctc | acggtcactt | 60 |
| gcttgtctga | ccgcaagtct | gcccatccct | ggggcagcca | actggcctca | gcccgtgccc | 120 |
| caggcgtgcc | ctgtctctgt | ctggctgccc | cagccctact | gtcttcctct | gtgtaggctc | 180 |
| tgcccagatg | cccggctggt | cctcagcctc | aggactatct | cagcagtgac | tcccctgatt | 240 |
| ctggacttgc | acctgactga | actcctgccc | acctcaaacc | ttcacctccc | accaccacca | 300 |
| ctccgagtcc | cgctgtgact | cccacgccca | ggagaccacc | caagtgcccc | agcctaaaga | 360 |
| atggctttct | gagaaagacc | ctgaaggagt | aggtctggga | cacagcatgc | cccggggccc | 420 |
| actggctgcc | ttactcctgc | tgattctcca | tggagcttgg | agctgcctgg | acctcacttg | 480 |
| ctacactgac | tacctctgga | ccatcacctg | tgtcctggag | acacggagcc | caaccccag | 540 |
| catactcagt | ctcacctggc | aagatgaata | tgaggaactt | caggaccaag | agaccttctg | 600 |
| cagcctacac | aggtctggcc | acaacaccac | acatatatgg | tacacgtgcc | atatgcgctt | 660 |
| gtctcaattc | ctgtccgatg | aagttttcat | tgtcaatgtg | acggaccagt | ctggcaacaa | 720 |
| ctcccaagag | tgtggcagct | ttgtcctggc | tgagagcatc | aaaccagctc | cccccttgaa | 780 |
| cgtgactgtg | gccttctcag | gacgctatga | tatctcctgg | gactcagctt | atgacgaacc | 840 |
| ctccaactac | gtgctgaggg | gcaagctaca | atatgagctg | cagtatcgga | acctcagaga | 900 |
| ccccctatgct | gtgaggccgg | tgaccaagct | gatctcagtg | gactcaagaa | acgtctctct | 960 |
| tctccctgaa | gagttccaca | agattctag | ctaccagctg | caggtgcggg | cagcgcctca | 1020 |
| gccaggcact | tcattcaggg | ggacctggag | tgagtggagt | gaccccgtca | tctttcagac | 1080 |
| ccaggctggg | gagcccgagg | caggctggga | ccctcacatg | ctgctgctcc | tggctgtctt | 1140 |
| gatcattgtc | ctggttttca | tgggtctgaa | gatccacctg | ccttggaggc | tatggaaaaa | 1200 |
| gatatgggca | ccagtgccca | cccctgagag | tttcttccag | cccctgtaca | gggagcacag | 1260 |
| cgggaacttc | aagaaatggg | ttaatacccc | tttcacggcc | tccagcatag | agttggtgcc | 1320 |
| acagagttcc | acaacaacat | cagccttaca | tctgtcattg | tatccagcca | aggagaagaa | 1380 |
| gttcccgggg | ctgccgggtc | tggaagagca | actggagtgt | gatggaatgt | ctgagcctgg | 1440 |
| tcactggtgc | ataatcccct | tggcagctgg | ccaagcggtc | tcagcctaca | gtgaggagag | 1500 |
| agaccggcca | tatggtctgg | tgtccattga | cacagtgact | gtgggagatg | cagagggcct | 1560 |
| gtgtgtctgg | ccctgtagct | gtgaggatga | tggctatcca | gccatgaacc | tggatgctgg | 1620 |
| ccgagagtct | ggccctaatt | cagaggatct | gctcttggtc | acagaccctg | cttttctgtc | 1680 |
| ttgcggctgt | gtctcaggta | gtggtctcag | gcttggaggc | tccccaggca | gcctactgga | 1740 |
| caggttgagg | ctgtcatttg | caaaggaagg | ggactggaca | gcagacccaa | cctggagaac | 1800 |
| tgggtcccca | ggaggggggct | ctgagagtga | agcaggttcc | cccctggtc | tggacatgga | 1860 |
| cacatttgac | agtggctttg | caggttcaga | ctgtggcagc | cccgtggaga | ctgatgaagg | 1920 |
| acccccctcga | agctatctcc | gccagtgggt | ggtcaggacc | cctccacctg | tggacagtgg | 1980 |
| agcccagagc | agctagcata | taataaccag | ctatagtgag | aagaggcctc | tgagcctggc | 2040 |
| atttacagtg | tgaacatgta | ggggtgtgtg | tgtgtgtgtg | tgtgtgtgtg | tgtgtgtgtg | 2100 |
| tgtgtgtgtg | tgtgtgtgtg | tgtcttgggt | tgtgtgttag | cacatccatg | ttgggatttg | 2160 |
| gtctgttgct | atgtattgta | atgctaaatt | ctctacccaa | agttctaggc | ctacgagtga | 2220 |
| attctcatgt | ttacaaactt | gctgtgtaaa | ccttgttcct | taatttaata | ccattggtta | 2280 |
| aataaaattg | gctgcaacca | attactggag | ggattagagg | tagggggctt | ttgagttacc | 2340 |

-continued

```
tgtttggaga tggagaagga gagaggagag accaagagga gaaggaggaa ggagaggaga    2400
ggagaggaga ggagaggaga ggagaggaga ggagaggaga ggctgccgtg              2460 agggagagg  gaccatgagc ctgtggccag gagaaacagc aagtatctgg ggtacactgg   2520
tgaggaggtg gccaggccag cagttagaag agtagattag gggtgacctc cagtatttgt   2580
caaagccaat taaataaca  aaaaaaaaaa aaaagcggcc gctctaga                2628
```

<210> SEQ ID NO 10
<211> LENGTH: 529
<212> TYPE: PRT
<213> ORGANISM: Mouse

<400> SEQUENCE: 10

```
Met Pro Arg Gly Pro Val Ala Ala Leu Leu Leu Ile Leu His Gly
 1               5                  10                  15

Ala Trp Ser Cys Leu Asp Leu Thr Cys Tyr Thr Asp Tyr Leu Trp Thr
                20                  25                  30

Ile Thr Cys Val Leu Glu Thr Arg Ser Pro Asn Pro Ser Ile Leu Ser
            35                  40                  45

Leu Thr Trp Gln Asp Glu Tyr Glu Glu Leu Gln Asp Gln Glu Thr Phe
        50                  55                  60

Cys Ser Leu His Arg Ser Gly His Asn Thr Thr His Ile Trp Tyr Thr
    65                  70                  75                  80

Cys His Met Arg Leu Ser Gln Phe Leu Ser Asp Glu Val Phe Ile Val
                85                  90                  95

Asn Val Thr Asp Gln Ser Gly Asn Asn Ser Gln Glu Cys Gly Ser Phe
            100                 105                 110

Val Leu Ala Glu Ser Ile Lys Pro Ala Pro Pro Leu Asn Val Thr Val
        115                 120                 125

Ala Phe Ser Gly Arg Tyr Asp Ile Ser Trp Asp Ser Ala Tyr Asp Glu
    130                 135                 140

Pro Ser Asn Tyr Val Leu Arg Gly Lys Leu Gln Tyr Glu Leu Gln Tyr
145                 150                 155                 160

Arg Asn Leu Arg Asp Pro Tyr Ala Val Arg Pro Val Thr Lys Leu Ile
                165                 170                 175

Ser Val Asp Ser Arg Asn Val Ser Leu Leu Pro Glu Glu Phe His Lys
            180                 185                 190

Asp Ser Ser Tyr Gln Leu Gln Val Arg Ala Ala Pro Gln Pro Gly Thr
        195                 200                 205

Ser Phe Arg Gly Thr Trp Ser Glu Trp Ser Asp Pro Val Ile Phe Gln
    210                 215                 220

Thr Gln Ala Gly Glu Pro Glu Ala Gly Trp Asp Pro His Met Leu Leu
225                 230                 235                 240

Leu Leu Ala Val Leu Ile Ile Val Leu Val Phe Met Gly Leu Lys Ile
                245                 250                 255

His Leu Pro Trp Arg Leu Trp Lys Lys Ile Trp Ala Pro Val Pro Thr
            260                 265                 270

Pro Glu Ser Phe Phe Gln Pro Leu Tyr Arg Glu His Ser Gly Asn Phe
        275                 280                 285

Lys Lys Trp Val Asn Thr Pro Phe Thr Ala Ser Ser Ile Glu Leu Val
    290                 295                 300

Pro Gln Ser Ser Thr Thr Thr Ser Ala Leu His Leu Ser Leu Tyr Pro
305                 310                 315                 320
```

-continued

```
Ala Lys Glu Lys Lys Phe Pro Gly Leu Pro Gly Leu Glu Glu Gln Leu
            325                 330                 335
Glu Cys Asp Gly Met Ser Glu Pro Gly His Trp Cys Ile Ile Pro Leu
            340                 345                 350
Ala Ala Gly Gln Ala Val Ser Ala Tyr Ser Glu Arg Asp Arg Pro
            355                 360                 365
Tyr Gly Leu Val Ser Ile Asp Thr Val Thr Val Gly Asp Ala Glu Gly
    370                 375                 380
Leu Cys Val Trp Pro Cys Ser Cys Glu Asp Gly Tyr Pro Ala Met
385                 390                 395                 400
Asn Leu Asp Ala Gly Arg Glu Ser Gly Pro Asn Ser Glu Asp Leu Leu
            405                 410                 415
Leu Val Thr Asp Pro Ala Phe Leu Ser Cys Gly Cys Val Ser Gly Ser
            420                 425                 430
Gly Leu Arg Leu Gly Gly Ser Pro Gly Ser Leu Leu Asp Arg Leu Arg
            435                 440                 445
Leu Ser Phe Ala Lys Glu Gly Asp Trp Thr Ala Asp Pro Thr Trp Arg
    450                 455                 460
Thr Gly Ser Pro Gly Gly Gly Ser Glu Ser Glu Ala Gly Ser Pro Pro
465                 470                 475                 480
Gly Leu Asp Met Asp Thr Phe Asp Ser Gly Phe Ala Gly Ser Asp Cys
            485                 490                 495
Gly Ser Pro Val Glu Thr Asp Glu Gly Pro Pro Arg Ser Tyr Leu Arg
            500                 505                 510
Gln Trp Val Val Arg Thr Pro Pro Val Asp Ser Gly Ala Gln Ser
            515                 520                 525
Ser
```

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 11
agcatcaagc cggctccccc                                           20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 12
ctccattcac tccaggtccc                                           20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 13
ttgaacgtga ctgrggcctt                                           20

<210> SEQ ID NO 14

-continued

```
<211> LENGTH: 20
<212> TYPE: DNA
<213> ORGANISM: Artificial Sequence
<220> FEATURE:
<223> OTHER INFORMATION: Description of Artificial Sequence: Murine MU-1
      cDNA internal Oligonucleotide

<400> SEQUENCE: 14
tgaatgaagt gcctggctga                                                  20

<210> SEQ ID NO 15
<211> LENGTH: 40
<212> TYPE: DNA
<213> ORGANISM: Artificial Sequence
<220> FEATURE:
<223> OTHER INFORMATION: Description of Artificial Sequence:
      5' PCR primer

<400> SEQUENCE: 15
cacaaagctt cagtatgagc tgcagtacag gaaccgggga                             40

<210> SEQ ID NO 16
<211> LENGTH: 40
<212> TYPE: DNA
<213> ORGANISM: Artificial Sequence
<220> FEATURE:
<223> OTHER INFORMATION: Description of Artificial Sequence:
      3' PCR primer

<400> SEQUENCE: 16
cacaggatcc ctttaactcc tctgactggg tctgaaagat                             40

<210> SEQ ID NO 17
<211> LENGTH: 224
<212> TYPE: PRT
<213> ORGANISM: Unknown Organism
<220> FEATURE:
<223> OTHER INFORMATION: Description of Unknown Organism: Second
      polypeptide comprising an Fc region

<400> SEQUENCE: 17
```

His Thr Cys Pro Pro Cys Pro Ala Pro Glu Ala Leu Gly Ala Pro Ser
 1               5                  10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Val Pro Ile Glu Lys Thr
            100                 105                 110

Ile Ser Lys Ala Lys Gly Gln Pro Arg Glu Pro Gln Val Tyr Thr Leu
        115                 120                 125

Pro Pro Ser Arg Glu Glu Met Thr Lys Asn Gln Val Ser Leu Thr Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp

-continued

```
                165                 170                 175
Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Lys
    210                 215                 220

<210> SEQ ID NO 18
<211> LENGTH: 617
<212> TYPE: DNA
<213> ORGANISM: Human

<400> SEQUENCE: 18
gctgaagtga aaacgagacc aaggtctagc tctactgttg gtacttatga gatccagtcc      60
tggcaacatg gagaggattg tcatctgtct gatggtcatc ttcttgggga cactggtcca     120
caaatcaagc tcccaaggtc aagatcgcca catgattaga atgcgtcaac ttatagatat     180
tgttgatcag ctgaaaaatt atgtgaatga cttggtccct gaatttctgc cagctccaga     240
agatgtagag acaaactgtg agtggtcagc tttttcctgc tttcagaagg cccaactaaa     300
gtcagcaaat acaggaaaca atgaaaggat aatcaatgta tcaattaaaa agctgaagag     360
gaaaccacct tccacaaatg cagggagaag acagaaacac agactaacat gcccttcatg     420
tgattcttat gagaaaaaac cacccaaaga attcctagaa agattcaaat cacttctcca     480
aaagatgatt catcagcatc tgtcctctag aacacacgga agtgaagatt cctgaggatc     540
taacttgcag ttggacacta tgttacatac tctaatatag tagtgaaagt catttctttg     600
tattccaagt ggaggag                                                   617

<210> SEQ ID NO 19
<211> LENGTH: 162
<212> TYPE: PRT
<213> ORGANISM: Human

<400> SEQUENCE: 19

Met Arg Ser Ser Pro Gly Asn Met Glu Arg Ile Val Ile Cys Leu Met
 1               5                  10                  15

Val Ile Phe Leu Gly Thr Leu Val His Lys Ser Ser Gln Gly Gln
            20                  25                  30

Asp Arg His Met Ile Arg Met Arg Gln Leu Ile Asp Ile Val Asp Gln
        35                  40                  45

Leu Lys Asn Tyr Val Asn Asp Leu Val Pro Glu Phe Leu Pro Ala Pro
    50                  55                  60

Glu Asp Val Glu Thr Asn Cys Glu Trp Ser Ala Phe Ser Cys Phe Gln
65                  70                  75                  80

Lys Ala Gln Leu Lys Ser Ala Asn Thr Gly Asn Asn Glu Arg Ile Ile
                85                  90                  95

Asn Val Ser Ile Lys Lys Leu Lys Arg Lys Pro Pro Ser Thr Asn Ala
            100                 105                 110

Gly Arg Arg Gln Lys His Arg Leu Thr Cys Pro Ser Cys Asp Ser Tyr
        115                 120                 125

Glu Lys Lys Pro Pro Lys Glu Phe Leu Glu Arg Phe Lys Ser Leu Leu
    130                 135                 140

Gln Lys Met Ile His Gln His Leu Ser Ser Arg Thr His Gly Ser Glu
145                 150                 155                 160
```

-continued

Asp Ser

<210> SEQ ID NO 20
<211> LENGTH: 7
<212> TYPE: PRT
<213> ORGANISM: Human

<400> SEQUENCE: 20

Glu Asp Asp Gly Tyr Pro Ala
 1               5

<210> SEQ ID NO 21
<211> LENGTH: 16
<212> TYPE: PRT
<213> ORGANISM: Unknown Organism
<220> FEATURE:
<223> OTHER INFORMATION: Description of Unknown Organism: Unknown

<400> SEQUENCE: 21

Met Pro Leu Leu Leu Leu Leu Leu Leu Pro Ser Pro Leu His Pro
 1               5                  10                  15

<210> SEQ ID NO 22
<211> LENGTH: 551
<212> TYPE: PRT
<213> ORGANISM: Homo sapiens

<400> SEQUENCE: 22

Met Ala Ala Pro Ala Leu Ser Trp Arg Leu Pro Leu Leu Ile Leu Leu
 1               5                  10                  15

Leu Pro Leu Ala Thr Ser Trp Ala Ser Ala Ala Val Asn Gly Thr Ser
            20                  25                  30

Gln Phe Thr Cys Phe Tyr Asn Ser Arg Ala Asn Ile Ser Cys Val Trp
        35                  40                  45

Ser Gln Asp Gly Ala Leu Gln Asp Thr Ser Cys Gln Val His Ala Trp
    50                  55                  60

Pro Asp Arg Arg Arg Trp Asn Gln Thr Cys Glu Leu Leu Pro Val Ser
65                  70                  75                  80

Gln Ala Ser Trp Ala Cys Asn Leu Ile Leu Gly Ala Pro Asp Ser Gln
                85                  90                  95

Lys Leu Thr Thr Val Asp Ile Val Thr Leu Arg Val Leu Cys Arg Glu
            100                 105                 110

Gly Val Arg Trp Arg Val Met Ala Ile Gln Asp Phe Lys Pro Phe Glu
        115                 120                 125

Asn Leu Arg Leu Met Ala Pro Ile Ser Leu Gln Val Val His Val Glu
    130                 135                 140

Thr His Arg Cys Asn Ile Ser Trp Glu Ile Ser Gln Ala Ser His Tyr
145                 150                 155                 160

Phe Glu Arg His Leu Glu Phe Glu Ala Arg Thr Leu Ser Pro Gly His
                165                 170                 175

Thr Trp Glu Glu Ala Pro Leu Leu Thr Leu Lys Gln Lys Gln Glu Trp
            180                 185                 190

Ile Cys Leu Glu Thr Leu Thr Pro Asp Thr Gln Tyr Glu Phe Gln Val
        195                 200                 205

Arg Val Lys Pro Leu Gln Gly Glu Phe Thr Thr Trp Ser Pro Trp Ser
    210                 215                 220

Gln Pro Leu Ala Phe Arg Thr Lys Pro Ala Ala Leu Gly Lys Asp Thr
225                 230                 235                 240

-continued

```
Ile Pro Trp Leu Gly His Leu Leu Val Gly Leu Ser Gly Ala Phe Gly
            245                 250                 255
Phe Ile Ile Leu Val Tyr Leu Leu Ile Asn Cys Arg Asn Thr Gly Pro
            260                 265                 270
Trp Leu Lys Lys Val Leu Lys Cys Asn Thr Pro Asp Pro Ser Lys Phe
            275                 280                 285
Phe Ser Gln Leu Ser Ser Glu His Gly Gly Asp Val Gln Lys Trp Leu
    290                 295                 300
Ser Ser Pro Phe Pro Ser Ser Ser Phe Ser Pro Gly Gly Leu Ala Pro
305                 310                 315                 320
Glu Ile Ser Pro Leu Glu Val Leu Glu Arg Asp Lys Val Thr Gln Leu
            325                 330                 335
Leu Leu Gln Gln Asp Lys Val Pro Glu Pro Ala Ser Leu Ser Ser Asn
            340                 345                 350
His Ser Leu Thr Ser Cys Phe Thr Asn Gln Gly Tyr Phe Phe Phe His
            355                 360                 365
Leu Pro Asp Ala Leu Glu Ile Glu Ala Cys Gln Val Tyr Phe Thr Tyr
    370                 375                 380
Asp Pro Tyr Ser Glu Glu Asp Pro Asp Glu Gly Val Ala Gly Ala Pro
385                 390                 395                 400
Thr Gly Ser Ser Pro Gln Pro Leu Gln Pro Leu Ser Gly Glu Asp Asp
            405                 410                 415
Ala Tyr Cys Thr Phe Pro Ser Arg Asp Asp Leu Leu Leu Phe Ser Pro
            420                 425                 430
Ser Leu Leu Gly Gly Pro Ser Pro Pro Ser Thr Ala Pro Gly Gly Ser
            435                 440                 445
Gly Ala Gly Glu Glu Arg Met Pro Pro Ser Leu Gln Glu Arg Val Pro
    450                 455                 460
Arg Asp Trp Asp Pro Gln Pro Leu Gly Pro Pro Thr Pro Gly Val Pro
465                 470                 475                 480
Asp Leu Val Asp Phe Gln Pro Pro Pro Glu Leu Val Leu Arg Glu Ala
            485                 490                 495
Gly Glu Glu Val Pro Asp Ala Gly Pro Arg Glu Gly Val Ser Phe Pro
            500                 505                 510
Trp Ser Arg Pro Pro Gly Gln Gly Glu Phe Arg Ala Leu Asn Ala Arg
            515                 520                 525
Leu Pro Leu Asn Thr Asp Ala Tyr Leu Ser Leu Gln Glu Leu Gln Gly
            530                 535                 540
Gln Asp Pro Thr His Leu Val
545                 550
```

METHODS OF TREATMENT WITH ANTAGONISTS OF MU-1

RELATED APPLICATIONS

This application is a continuation-in-part of U.S. Ser. No. 09/569,384, filed May 11, 2000; U.S. Ser. No. 09/560,766, filed Apr. 28, 2000 now abandoned; and U.S. Ser. No. 09/040,005, Mar. 17, 1998, which is now issued as U.S. Pat. No. 6,057,128.

FIELD OF THE INVENTION

The present invention relates to new members of the mammalian cytokine receptor family of proteins (including without limitation human and murine receptor proteins), fragments thereof and recombinant polynucleotides and cells useful for expressing such proteins.

BACKGROUND OF THE INVENTION

A variety of regulatory molecules, known as hematopoietins been identified which are involved in the development and proliferation of the various populations of hematopoietic or blood cells. Most hematopoietins exhibits certain biological activities by interacting with a receptor on the surface of target cells. Cytokine receptors are commonly composed of one, two or three chains. Many cytokine receptors and some cytokines, such as IL-12 p40, are members of the hematopoietin receptor superfamily of proteins. Identification of new members of the hematopoietin receptor superfamily can be useful in regulation of hematopoiesis, in regulation of immune responses and in identification of other members of the hematopoietin superfamily, including cytokines and receptors.

It would be desirable to identify and determine the DNA and protein sequence for heretofore unknown members of the hematopoietin receptor superfamily.

SUMMARY OF THE INVENTION

In accordance with the present invention, polynucleotides encoding the MU-1 hematopoietin receptor superfamily chain are disclosed, including without limitation those from the murine and human sources. The MU-1 polypeptide is also known as the IL-21 receptor polypeptide.

In certain embodiments, the invention provides an isolated polynucleotide comprising a nucleotide sequence selected from the group consisting of:
(a) the nucleotide sequence of SEQ ID NO:1;
(b) the nucleotide sequence of SEQ ID NO:1 from nucleotide 238 to nucleotide 1852;
(c) the nucleotide sequence of SEQ ID NO:1 from nucleotide 301 to nucleotide 1852;
(d) the nucleotide sequence of SEQ ID NO:1 from nucleotide 301 to nucleotide 945;
(e) a nucleotide sequence varying from the sequence of the nucleotide sequence specified in any of (a)–(d) as a result of degeneracy of the genetic code;
(f) a nucleotide sequence capable of hybridizing under stringent conditions to the nucleotide specified in any of (a)–(d);
(g) a nucleotide sequence encoding a species homologue of the sequence of SEQ ID NO:2; and
(h) an allelic variant of the nucleotide sequence specified in any of (a)–(d).

Preferably, the nucleotide sequence encodes a protein having a biological activity of the MU-1 hematopoietin receptor superfamily chain. The nucleotide sequence may be operably linked to an expression control sequence.

The invention also provides isolated polynucleotides comprising a nucleotide sequence encoding a peptide or protein comprising an amino acid sequence selected from the group consisting of:
(a) the amino acid sequence of SEQ ID NO:2;
(b) the amino acid sequence of SEQ ID NO:2 from amino acids 22 to 538;
(c) the amino acid sequence of SEQ ID NO:2 from amino acids 22 to 236;
(d) the amino acid sequence of SEQ ID NO:2 from amino acids 1 to 236; and
(e) fragments of (a)–(d) having a biological activity of the MU-1 hematopoietin receptor superfamily chain.

Host cells, preferably mammalian cells, transformed with the polynucleotides are also provided.

In other embodiments, the invention provides a process for producing a MU-1 protein.

The process comprises:
(a) growing a culture of the host cell of the present invention in a suitable culture medium; and
(b) purifying the human MU-1 protein from the culture. Proteins produced according to these methods are also provided.

The present invention also provides for an isolated MU-1 protein comprising an amino acid sequence selected from the group consisting of:
(a) the amino acid sequence of SEQ ID NO:2;
(b) the amino acid sequence of SEQ ID NO:2 from amino acids 22 to 538;
(c) the amino acid sequence of SEQ ID NO:2 from amino acids 22 to 236;
(d) the amino acid sequence of SEQ ID NO:2 from amino acids 1 to 236; and
(e) fragments of (a)–(d) having a biological activity of the MU-1 hematopoietin receptor superfamily chain. In other preferred embodiments, the specified amino acid sequence is part of a fusion protein (with an additional amino acid sequence not derived from MU-1).

The invention also provides a fusion polypeptide comprising at least a fragment of an MU-1 polypeptide and a non-MU-1 fusion polypeptide. At least a fragment of an MU-1 polypeptide has the biological activity of a MU-1 hematopoietin receptor superfamily chain. In some embodiments, the MU-1 portion of the fusion polypeptide is a full-length MU-1 polypeptide.

In other embodiments, the MU-1 portion is a fragment of a MU-1 polypeptide and has the biological activity of a MU-1 hematopoietin receptor superfamily chain. For example, the fusion polypeptide can include a soluble form of a MU-1 polypeptide.

Preferred fusion proteins comprise an antibody fragment, such as an Fc fragment, i.e., the non-MU-1 polypeptide is preferably an antibody fragment. The antibody fragment can be, e.g., a Fc fragment.

Alternatively, or in addition, the non-MU-1 polypeptide can be a GST, Lex-A or MBP polypeptide sequence.

If desired the fusion polypeptide may further include a linker sequence.

In some embodiments, the MU-1 polypeptide in the fusion polypeptide includes amino acids 22–236 of SEQ ID NO:2, e.g., the polypeptide can include amino acids 22–538 of SEQ ID NO:2. In other embodiments, the MU-1 polypeptide includes amino acids 20–253 of SEQ ID NO:10.

In a preferred embodiment, the fusion polypeptide includes amino acids 20–236 of SEQ ID NO:2 operably linked to an Fc fragment. The fusion polypeptide may optionally include a linker sequence. Preferably, the fusion polypeptide includes amino acids 20–538 of SEQ ID NO:2.

Pharmaceutical compositions comprising a protein of the present invention and a pharmaceutically acceptable carrier are also provided. For example, the invention includes a pharmaceutical composition that includes a pharmaceutically acceptable carrier and a fusion polypeptide comprising at least a fragment of an MU-1 polypeptide and a non-MU-1 fusion polypeptide. The MU-1 polypeptide has the biological activity of a MU-1 hematopoietin receptor superfamily chain.

The fusion polypeptide in the composition preferably includes a soluble form of a MU-1 polypeptide.

The non-MU-1 polypeptide in the composition preferably is an antibody fragment, e.g., an Fc fragment.

In a preferred embodiment, the pharmaceutical composition includes a pharmaceutically acceptable carrier and fusion polypeptide that includes amino acids 20–236 of SEQ ID NO:2 operably linked to an Fc fragment.

The present invention further provides for compositions comprising an antibody which specifically reacts with a protein of the present invention.

The invention also provides a method for inhibiting T-cell proliferation by contacting a population of T cells with a MU-1 polypeptide antagonist in an amount sufficient to inhibit proliferation of the T-cell population. In some embodiments, the T cell population is a substantially purified population of T cells.

The antagonist can be, e.g., an IL-21 fusion protein, an IL-21 antibody, an IL-21 receptor antibody.

The T cells can be, e.g., $CD8_+$ cells, $CD4_+$ cells, or lymph node T cells, thymocytes, and anti-CD3-induced proliferating thymocytes.

The invention also provides a method for enhancing T-cell proliferation by contacting a population of T cells with an agent that increases MU-1 polypeptide levels in an amount sufficient to enhance proliferation of the T-cells. The IL-21R antagonists can be additionally be used to treat or prevent undesired immune responses associated with autoimmune disorders or organ transplantation.

In some embodiments, the T cell population is a substantially purified population of T cells. The agent can be, e.g., an IL-21 protein (such as a polypeptide that includes the amino acid sequence of a human IL-21 protein). Alternatively, in some embodiments, the agent is a nucleic acid encoding an IL-21 polypeptide.

The T cells can be, e.g., $CD8_+$ cells, $CD4_+$ cells, lymph node T cells, thymocytes, and anti-CD3-induced proliferating thymocytes.

Also provided by the invention are methods for enhancing an immune response by adding an agent that increases levels of IL-21 in a subject (e.g., a human, non-human primate, or rodent). The agent is preferably designed to increase the immune response to a cancer or infectious disease. The infectious disease can be caused by, e.g., bacterial or viral agents. If desired, the agent that increases levels of IL-21 can be administered in conjunction with one or more additional agents that increase an immune response, e.g., an agent that enhances an immune response to a cancer or infectious disease, in the subject.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIGS. 1A and 1B depicts the full-length cDNA sequence of murine MU-1. The nucleotide sequence corresponds to nucleotides 1–2628 of SEQ ID NO:9.

FIG. 2 depicts the amino acid sequence of murine MU-1 (corresponding to the amino acids 1–529 of SEQ ID NO:10). There is a predicted leader sequence at amino acids 1–19, which was predicted by SPScan with score of 10.1 (bold-face type). There is a predicted transmembrane domain at amino acids 237–253 (underlined). Predicted signaling motifs include the following regions: Box 1: amino acids 265–274 and Box 2: amino acids 310–324 (bold and underlined); Six Tyrosine's are located at amino acid positions 281, 319, 361, 368, 397, and 510. The WSXWS motif (SEQ ID NO:8) is located at amino acid residue 214 to amino acid residue 218 (in large, bold-face type). Potential STAT docking sites include, amino acids 393–398 and amino acids 510–513.

FIGS. 3A–D depicts the GAP comparison of human and murine MU-1cDNA sequences (corresponding to nucleic acids 1–2665 of SEQ ID NO:1 and nucleic acids 1–2628 of SEQ ID NO:9, respectively). HuMU-1=human MU-1, murMU-1=murine MU-1. Gap Parameters: Gap Weight=50, Average Match=10.000, Length Weight=3, Average Mismatch=0.000. Percent Identity=66.116.

FIG. 4 depicts a GAP comparison of the human MU-1 protein (corresponding to amino acids 1–538 of SEQ ID NO:2) and the murine MU-1 protein (corresponding to amino acids 1–529 of SEQ ID NO:10). BLOSUM62 amino acid substitution matrix. (Henikoff, S. and Henikoff, J. G. (1992)). Amino acid substitution matrices from protein blocks (Proc. Natl. Acad. Sci. USA 89: 10915–10919). Gap parameters=Gap Weight:8, Average Match=2.9 12, Length Weight=2, Average Mismatch=−2.003. Percent Identity=65.267.

FIG. 5 depicts a multiple sequence alignment of the amino acids of human MU-1 (corresponding to SEQ ID NO:2), murine MU-1 (corresponding to SEQ ID NO:10), and human IL2beta chain (GENbank Accession No. M26062) (SEQ ID NO:22). Leader and transmembrane domains are underlined. Conserved cytokine receptor module motifs are indicated by bold-face type. Potential signaling regions are indicated by underlining and bold-face type.

DETAILED DESCRIPTION OF THE INVENTION

Figure 6:
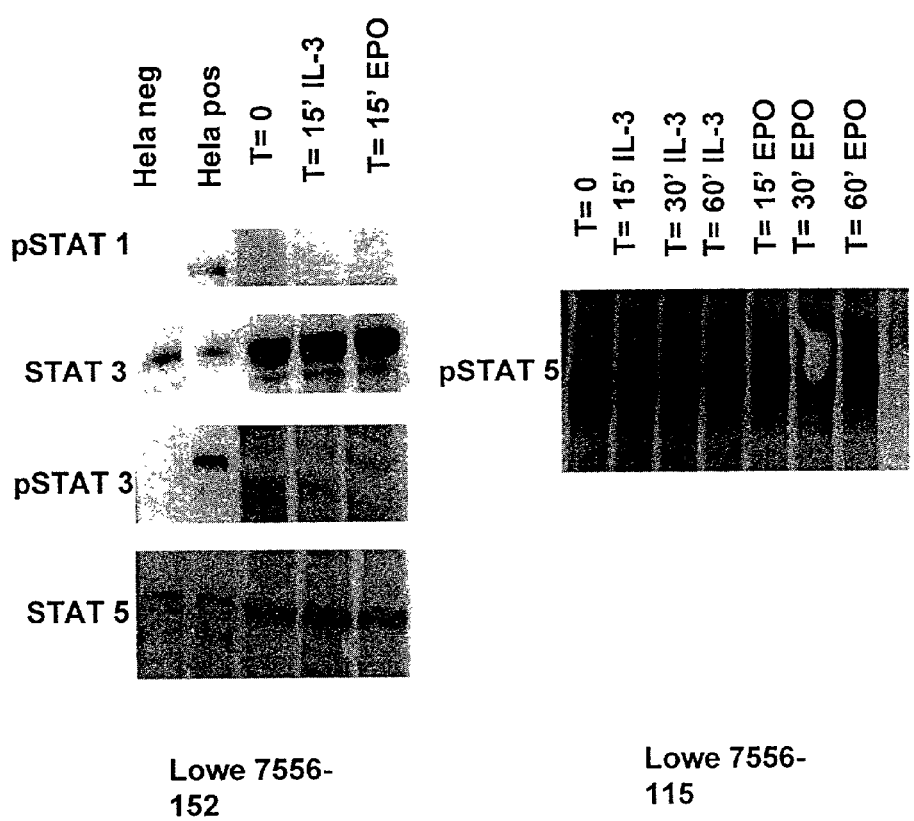
FIG. 6 depicts signaling through MU-1. MU-1 phosphorylates STAT 5 in Clone E7 EPO-MU-1 chimera. Under the conditions specified in Example 3, signaling through MU-1 results in the phosphorylation of STAT 5 at all time-points tested. Treatment of controls or the chimeric BAF-3 cells with IL-3 resulted in phosphorylation of STAT 3, but not STAT 1 or5.

The inventors of the present application have for the first time identified and provided polynucleotides encoding the MU-1 hematopoietin receptor superfamily chain (hereinafter "MU-1" or "MU-1 protein"), including without limitation polynucleotides encoding human MU-1. A 70 amino acid region of the human IL5 receptor (LMTNAFISIIDDL-SKYDVQVRAAVSSMCREAGLWSEWS-QPIYVGNDEHKPLREWFVIVI MATICFILLIL, SEQ ID NO:3) was used to search the GenBank EST database using the TBLASTN algorithm. Sequence within the genomic BAC clone AC002303 from human chromosome 16p12 was identified with homology to this region, suggesting that this segment might encode a gene for a novel hematopoietin receptor. Examination of open reading frames within 1000 bp of nucleotide 40,886 revealed a 270 bp open frame which when used in a BLASTP search of GenPept exclusively identified members of the cytokine receptor family. A stop codon present at the end of this reading frame was interpreted as indication of transition over an exon/intron border.

It was then determined whether RNA was transcribed from a gene contained within this BAC clone from chromosome 16p12. PCR primers were synthesized based on the largest ORF segment which contained peptide sequence conserved within the cytokine receptor family. Primers GAGTCCGAGGAGAAAGCTGATCTCA (5p) (SEQ ID NO:4) and GAAAGATGACCGGGTCACTCCATT (3p) (SEQ ID NO:5) were used in PCRs to screen phage libraries from various human tissues (Clontech). PCR products of the expected 164 bp size which specifically hybridized to a 32-P labeled oligonucleotide of the sequence ACTCGAGCTAT-GAGCTGCAGGTGCGGGCA (SEQ ID NO:6) were observed in phage from lung, kidney, placenta and heart. Using the oligonucleotide ACTCGAGCTATGAGCTG-CAGGTGCGGGCA (SEQ ID NO:7) a full-length cDNA clone NN14-1b (MU-1) was identified, purified, and sequenced. The DNA sequence and the predicted amino acid sequence are shown in SEQ ID NO:1 and SEQ ID NO:2, respectively. The open reading frame encodes a novel member of the hematopoietin receptor family. It has a leader sequence, conserved cysteine pairs, PP, and WSXWS (SEQ ID NO:8) motifs characteristic of the family as well as a transmembrane domain and extensive cytoplasmic domain. Subsequent FASTA alignment of this sequence with Gen-Pept showed greatest homology with human IL-2Rb. The predicted amino acid sequence of the receptor chain includes a putative signal sequence from amino acids 1–21. The mature human MU-1 is believed to have the sequence of amino acids 24–538 of SEQ ID NO:2. A transmembrane domain is found at amino acids 237–254.

The MU-1 cDNA was deposited with the American Type Culture Collection on Mar. 10, 1998, as accession number ATCC 98687. Any forms of MU-1 proteins of less than full length are encompassed within the present invention and are referred to herein collectively with full length and mature forms as "MU-1" or "MU-1 proteins." MU-1 proteins of less than full length may be produced by expressing a corresponding fragment of the polynucleotide encoding the full-length MU-1 protein (SEQ ID NO:4 or SEQ ID NO:6). These corresponding polynucleotide fragments are also part of the present invention. Modified polynucleotides as described above may be made by standard molecular biology techniques, including construction of appropriate desired deletion mutants, site-directed mutagenesis methods or by the polymerase chain reaction using appropriate oligonucleotide primers.

For the purposes of the present invention, a protein has "a biological activity of the MU-1 hematopoietin receptor superfamily chain" if it possess one or more of the biological activities of the corresponding mature MU-1 protein.

MU-1 or active fragments thereof (MU-1 proteins) may be fused to carrier molecules such as immunoglobulins. For example, soluble forms of the MU-1 may be fused through "linker" sequences to the Fc portion of an immunoglobulin. Other fusions proteins, such as those with GST, Lex-A or MBP, may also be used.

In a further embodiment, the MU-1 fusion protein may be linked to one or more additional moieties. For example, the MU-1 fusion protein may additionally be linked to a GST fusion protein in which the Mu-1 fusion protein sequences are fused to the C-terminus of the GST (i.e., glutathione S-transferase) sequences. Such fusion proteins can facilitate the purification of the MU-1 fusion protein.

In another embodiment, the fusion protein is includes a heterologous signal sequence (i.e., a polypeptide sequence that is not present in a polypeptide encoded by a Mu-1 nucleic acid) at its N-terminus. For example, the native Mu-1 signal sequence can be removed and replaced with a signal sequence from another protein. In certain host cells (e.g., mammalian host cells), expression and/or secretion of Mu-1 can be increased through use of a heterologous signal sequence.

A chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) CURRENT PROTOCOLS IN MOLECULAR BIOLOGY, John Wiley & Sons, 1992). Moreover, many expression vectors are commercially available that encode a fusion moiety (e.g., an Fc region of an immunoglobulin heavy chain). A Mu-1 encoding nucleic acid can be cloned into such an expression vector such that the fusion moiety is linked in-frame to the immunoglobulin protein.

In some embodiments, mu-1 fusion polypeptides exist as oligomers, such as dimers or trimers.

The first polypeptide, and/or nucleic acids encoding the first polypeptide, can be constructed using methods known in the art.

In some embodiments, the Mu-1 polypeptide moiety is provided as a variant Mu-1 polypeptide having a mutation in the naturally-occurring Mu-1 sequence (wild type) that results in higher affinity (relative to the non-mutated sequence) binding of the Mu-1 polypeptide to a IL-21.

In some embodiments, the Mu-1 polypeptide moiety is provided as a variant Mu-1 polypeptide having mutations in the naturally-occurring Mu-1 sequence (wild type) that results in a Mu-1 sequence more resistant to proteolysis (relative to the non-mutated sequence).

In some embodiments, the first polypeptide includes full-length Mu-1 polypeptide. Alternatively, the first polypeptide comprise less than full-length Mu-1 polypeptide.

A signal peptide that can be included in the fusion protein is MPLLLLLLLLPSPLHP (SEQ ID NO:21). If desired, one or more amino acids can additionally be inserted between the first polypeptide moiety comprising the Mu-1 moiety and the second polypeptide moiety.

The second polypeptide is preferably soluble. In some embodiments, the second polypeptide enhances the half-life, (e.g., the serum half-life) of the linked polypeptide. In some embodiments, the second polypeptide includes a sequence that facilitates association of the fusion polypeptide with a second Mu-1 polypeptide. In preferred embodiments, the second polypeptide includes at least a region of an immunoglobulin polypeptide. Immunoglobulin fusion polypeptide are known in the art and are described in e.g., U.S. Pat. Nos. 5,516,964; 5,225,538; 5,428,130;5,514,582; 5,714,147; and 5,455,165.

In some embodiments, the second polypeptide comprises a full-length immunoglobulin polypeptide. Alternatively, the second polypeptide comprise less than full-length immunoglobulin polypeptide, e.g., a heavy chain, light chain, Fab, Fab$_2$, Fv, or Fc. Preferably, the second polypeptide includes the heavy chain of an immunoglobulin polypeptide. More preferably, the second polypeptide includes the Fc region of an immunoglobulin polypeptide.

In another aspect of the invention the second polypeptide has less effector function that the effector function of a Fc region of a wild-type immunoglobulin heavy chain. Fc effector function includes for example, Fc receptor binding, complement fixation and T cell depleting activity. (see for example, U.S. Pat. No. 6,136,310) Methods of assaying T cell depleting activity, Fc effector function, and antibody stability are known in the art. In one embodiment the second polypeptide has low or no affinity for the Fc receptor. In an alternative embodiment, the second polypeptide has low or no affinity for complement protein C1q.

A preferred second polypeptide sequence includes the amino acid sequence of SEQ ID NO: 17. This sequence includes a Fc region. Underlined amino acids are those that differ from the amino acid found in the corresponding position of the wild-type immunoglobulin sequence:

```
                                              (SEQ ID NO:17)
HTCPPCPAPEALGAPSVFLFPPKPKDTLMISRTPEVTCVVVDVSHEDPEV

KFNWYVDGVEVHNAKTKPREEQYNSTYRVVSVLTVLHQDWLNGKEYKCKV

SNKALPVPIEKTISKAKGQPREPQVYTLPPSREEMTKNQVSLTCLVKGFY

PSDIAVEWESNGQPENNYKTTPPVLDSDGSFFLYSKLTVDKSRWQQGNVF

SCSVMHEALHNHYTQKSLSLSPGK
```

The invention also encompasses allelic variants of the nucleotide sequence as set forth in SEQ ID NO:1, that is, naturally-occurring alternative forms of the isolated polynucleotide of SEQ ID NO:1 which also encode MU-1 proteins, preferably those proteins having a biological activity of MU-1. Also included in the invention are isolated polynucleotides which hybridize to the nucleotide sequence set forth in SEQ ID NO:1 under highly stringent conditions (for example, 0.1×SSC at 65° C.). Isolated polynucleotides which encode MU-1 proteins but which differ from the nucleotide sequence set forth in SEQ ID NO:1 by virtue of the degeneracy of the genetic code are also encompassed by the present invention. Variations in the nucleotide sequence as set forth in SEQ ID NO:1 which are caused by point mutations or by induced modifications are also included in the invention.

The present invention also provides polynucleotides encoding homologues of the human MU-1 from other animal species, particularly other mammalian species. Species homologues can be identified and isolated by making probes or primers from the murine or human sequences disclosed herein and screening a library from an appropriate species, such as for example libraries constructed from PMTs, thymus or testis of the relevant species. The isolated polynucleotides of the invention may be operably linked to an expression control sequence such as the pMT2 or pED expression vectors disclosed in Kaufman et al., Nucleic Acids Res. 19, 4485–4490 (1991), in order to produce the MU-1 protein recombinantly. Many suitable expression control sequences are known in the art. General methods of expressing recombinant proteins are also known and are exemplified in R. Kaufman, Methods in Enzymology 185, 537–566 (1990). As defined herein "operably linked" means enzymatically or chemically ligated to form a covalent bond between the isolated polynucleotide of the invention and the expression control sequence, in such a way that the MU-1 protein is expressed by a host cell which has been transformed (transfected) with the ligated polynucleotide/expression control sequence.

A number of types of cells may act as suitable host cells for expression of the MU-1 protein. Any cell type capable of expressing functional MU-1 protein may be used. Suitable mammalian host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK, Rat2, BaF3, 32D, FDCP-1, PC12, M1x or C2C12 cells.

The MU-1 protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif. U.S.A. (the MaxBac® kit), and such methods are well known in the art, as described in Summers and Smith, Texas Agricultural Experiment Station Bulletin No. 1555 (1987), incorporated herein by reference. Soluble forms of the MU-1 protein may also be produced in insect cells using appropriate isolated polynucleotides as described above. Alternatively, the MU-1 protein may be produced in lower eukaryotes such as yeast or in prokaryotes such as bacteria. Suitable yeast strains include *Saccharomyces cerevisiae, Schizosaccharomyces pombe, Kluyveromyces* strains, *Candida*, or any yeast strain capable of expressing heterologous proteins. Suitable bacterial strains include *Escherichia coli, Bacillus subtilis, Salmonella typhimurium*, or any bacterial strain capable of expressing heterologous proteins.

Expression in bacteria may result in formation of inclusion bodies incorporating the recombinant protein. Thus, refolding of the recombinant protein may be required in order to produce active or more active material. Several methods for obtaining correctly folded heterologous proteins from bacterial inclusion bodies are known in the art. These methods generally involve solubilizing the protein from the inclusion bodies, then denaturing the protein completely using a chaotropic agent. When cysteine residues are present in the primary amino acid sequence of the protein, it is often necessary to accomplish the refolding in an environment which allows correct formation of disulfide bonds (a redox system). General methods of refolding are disclosed in Kohno, Meth. Enzym., 185:187–195 (1990). EP 0433225 and copending application U.S. Ser. No. 08/163,877 describe other appropriate methods. The MU-1 protein of the invention may also be expressed as a product of transgenic animals, e.g., as a component of the milk of transgenic cows, goats, pigs, or sheep which are characterized by somatic or germ cells containing a polynucleotide sequence encoding the MU-1 protein. The MU-1 protein of the invention may be prepared by growing a culture transformed host cells under culture conditions necessary to express the desired protein. The resulting expressed protein may then be purified from the culture medium or cell extracts. Soluble forms of the MU-1 protein of the invention can be purified from conditioned media. Membrane-bound forms of MU-1 protein of the invention can be purified by preparing a total membrane fraction from the expressing cell and extracting the membranes with a non-ionic detergent such as Triton X-100. The MU-1 protein can be purified using methods known to those skilled in the art. For example, the MU-1 protein of the invention can be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) or polyetheyleneimine (PEI) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred (e.g., S-Sepharose® columns). The purification of the MU-1 protein from culture supernatant may also include one or more column steps over such affinity resins as concanavalin A-agarose, heparin-toyopearl® or Cibacrom blue 3GA Sepharose®; or by hydrophobic interaction chromatography using such resins as phenyl ether, butyl ether, or propyl ether; or by immunoaffinity chromatography. Finally, one or more reverse-phase high performance liquid chromatography (RP-HPLC) steps employing hydrophobic RP-HPLC media, e.g., silica gel having pendant methyl or other aliphatic groups, can be employed to further purify the MU-1 protein. Affinity columns including antibodies to the MU-1 protein can also be used in purification in accordance with known methods. Some or all of the foregoing purification steps, in various combinations or with other known methods, can also be employed to provide a substantially purified isolated recombinant protein. Preferably, the isolated MU-1 protein is purified so that it is substantially free of other mammalian proteins.

MU-1 proteins of the invention may also be used to screen for agents which are capable of binding to MU-1. Binding assays using a desired binding protein, immobilized or not, are well known in the art and may be used for this purpose using the MU-1 protein of the invention. Purified cell based or protein based (cell free) screening assays may be used to identify such agents. For example, MU-1 protein may be immobilized in purified form on a carrier and binding or potential ligands to purified MU-1 protein may be measured.

MU-1 proteins, purified from cells or recombinantly produced, may be used as a pharmaceutical composition when combined with a pharmaceutically acceptable carrier. Such a composition may contain, in addition to MU-1 or inhibitor and carrier, various diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration.

The pharmaceutical composition of the invention may also contain cytokines, lymphokines, or other hematopoietic factors such as M-CSF, GM-CSF, IL-1, IL-2, IL-3, IL-4, IL-5, IL -6, IL-7, IL-8, IL-9, IL-10, IL-11, IL-12, IL-14, IL-15, G-CSF, stem cell factor, and erythropoietin. The pharmaceutical composition may also include anti-cytokine antibodies. The pharmaceutical composition may contain thrombolytic or anti-thrombotic factors such as plasminogen activator and Factor VIII. The pharmaceutical composition may further contain other anti-inflammatory agents. Such additional factors and/or agents may be included in the pharmaceutical composition to produce a synergistic effect with isolated MU-1 protein, or to minimize side effects caused by the isolated MU-1 protein. Conversely, isolated MU-1 protein may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

The pharmaceutical composition of the invention may be in the form of a liposome in which isolated MU-1 protein is combined, in addition to other pharmaceutically acceptable carriers, with amphipathic agents such as lipids which exist in aggregated form as micelles, insoluble monolayers, liquid crystals, or lamellar layers which in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

As used herein, the term "therapeutically effective amount" means the total amount of each active component of the pharmaceutical composition or method that is sufficient to show a meaningful patient benefit, e.g., amelioration of symptoms of, healing of, or increase in rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of isolated MU-1 protein is administered to a mammal. Isolated MU-1 protein may be administered in accordance with the method of the invention either alone or in combination with other therapies such as treatments employing cytokines, lymphokines or other hematopoietic factors. When co-administered with one or more cytokines, lymphokines or other hematopoietic factors, MU-1 protein may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering MU-1 protein in combination with cytokine(s), lymphokine(s), other hematopoietic factor(s), thrombolytic or anti-thrombotic factors. Administration of MU-1 protein used in the pharmaceutical composition or to practice the method of the present invention can be carried out in a variety of conventional ways, such as oral ingestion, inhalation, or cutaneous, subcutaneous, or intravenous injection. Intravenous administration to the patient is preferred.

When a therapeutically effective amount of MU-1 protein is administered orally, MU-1 protein will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% MU-1 protein, and preferably from about 25 to 90% MU-1 protein. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of MU-1 protein, and preferably from about 1 to 50% MU-1 protein.

When a therapeutically effective amount of MU-1 protein is administered by intravenous, cutaneous or subcutaneous injection, MU-1 protein will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to MU-1 protein an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additive known to those of skill in the art.

The amount of MU-1 protein in the pharmaceutical composition of the present invention will depend upon the nature and severity of the condition being treated, and on the nature of prior treatments which the patient has undergone. Ultimately, the attending physician will decide the amount of MU-1 protein with which to treat each individual patient. Initially, the attending physician will administer low doses of MU-1 protein and observe the patient's response. Larger doses of MU-1 protein may be administered until the optimal therapeutic effect is obtained for the patient, and at that point the dosage is not generally increased further. It is contemplated that the various pharmaceutical compositions used to practice the method of the present invention should contain about 0.1 μg to about 100 mg of MU-1 protein per kg body weight.

The duration of intravenous therapy using the pharmaceutical composition of the present invention will vary, depending on the severity of the disease being treated and the condition and potential idiosyncratic response of each individual patient. It is contemplated that the duration of each application of the MU-1 protein will be in the range of 12 to 24 hours of continuous intravenous administration. Ultimately the attending physician will decide on the appropriate duration of intravenous therapy using the pharmaceutical composition of the present invention. The polynucleotide and proteins of the present invention are expected to exhibit one or more of the uses or biological activities (including those associated with assays cited herein) identified below. Uses or activities described for proteins of the present invention may be provided by administration or use of such proteins or by administration or use of polynucleotides encoding such proteins (such as, for example, in gene therapies or vectors suitable for introduction of DNA).

Cytokine and Cell Proliferation/Differentiation Activity

A protein of the present invention may exhibit cytokine, cell proliferation (either inducing or inhibiting) or cell differentiation (either inducing or inhibiting) activity or may induce production of other cytokines in certain cell populations. Many protein factors discovered to date, including all known cytokines, have exhibited activity in one or more factor dependent cell proliferation assays, and hence the assays serve as a convenient confirmation of cytokine activity. The activity of a protein of the present invention is evidenced by any one of a number of routine factor dependent cell proliferation assays for cell lines including, without limitation, 32D, DA2, DA1G, T10, B9, B9/11, BaF3,MC9/G, M+(preB M+), 2E8, RB5, DA1, 123, T1165, HT2, CTLL2, TF-1, Mo7e and CMK.

The activity of a protein of the invention may, among other means, be measured by the following methods:

Assays for T-cell or thymocyte proliferation include without limitation those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Bertagnolli et al., J. Immunol. 145:1706–1712, 1990; Bertagnolli et al., Cellular Immunology 133:327–341, 1991; Bertagnolli, et al., J. Immunol. 149:3778–3783, 1992; Bowman et al., J. Immunol. 152: 1756–1761, 1994. Assays for cytokine production and/or proliferation of spleen cells, lymph node cells or thymocytes include, without limitation, those described in: Polyclonal T cell stimulation, Kruisbeek, A. M. and Shevach, E. M. In Current Protocols in Immunology. J. E. e.a. Coligan eds. Vol I pp. 3.12.1–3.12.14, John Wiley and Sons, Toronto. 1994; and Measurement of mouse and human Interferon .gamma., Schreiber, R. D. In Current Protocols in Immunology. J. E. e.a. Coligan eds. Vol 1 pp. 6.8.1–6.8.8, John Wiley and Sons, Toronto. 1994.

Assays for proliferation and differentiation of hematopoietic and lymphopoietic cells include, without limitation, those described in: Measurement of Human and Murine Interleukin 2 and Interleukin 4, Bottomly, K., Davis, L. S. and Lipsky, P. E. In Current Protocols in Immunology. J. E. e.a. Coligan eds. Vol 1 pp. 6.3.1–6.3.12, John Wiley and Sons, Toronto. 1991; deVries et al., J. Exp. Med. 173: 1205–1211, 1991; Moreau et al., Nature 336:690–692, 1988; Greenberger et al., Proc. Natl. Acad. Sci. U.S.A. 80:2931–2938, 1983; Measurement of mouse and human interleukin 6—Nordan, R. In Current Protocols in Immunology. J. E. e.a. Coligan eds. Vol 1 pp. 6.6.1–6.6.5, John Wiley and Sons, Toronto. 1991; Smith et al., Proc. Natl. Acad. Sci. U.S.A. 83:1857–1861, 1986; Measurement of humanInterleukin 11—Bennett, F., Giannotti, J., Clark, S. C. and Turner, K. J. In Current Protocols in Immunology. J. E. e.a. Coligan eds. Vol 1 pp. 6.15.1 John Wiley and Sons, Toronto. 1991; Measurement of mouse and human Interleukin 9—Ciarletta, A., Giannotti, J., Clark, S. C. and Turner, K. J. In Current Protocols in Immunology. J. E. e.a. Coligan eds. Vol 1 pp. 6.13.1, John Wiley and Sons, Toronto. 1991.

Assays for T-cell clone responses to antigens (which will identify, among others, proteins that affect APC-T cell interactions as well as direct T-cell effects by measuring proliferation and cytokine production) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function; Chapter 6, Cytokines and their cellular receptors; Chapter 7, Immunologic studies in Humans); Weinberger et al., Proc. Natl. Acad. Sci. U.S.A. 77:6091–6095, 1980; Weinberger et al., Eur. J. Immun. 11:405–411, 1981; Takai et al., J. Immunol. 137:3494–3500, 1986; Takai et al., J. Immunol. 140:508–512, 1988.

Immune Stimulating or Suppressing Activity

A protein of the present invention may also exhibit immune stimulating or immune suppressing activity, including without limitation the activities for which assays are described herein. A protein may be useful in the treatment of various immune deficiencies and disorders (including severe combined immunodeficiency (SCID)), e.g., in regulating (up or down) growth and proliferation of T and/or B lymphocytes, as well as effecting the cytolytic activity of NK cells and other cell populations. These immune deficiencies may be genetic or be caused by viral (e.g., HIV) as well as bacterial or fungal infections, or may result from autoimmune disorders. More specifically, infectious diseases causes by viral, bacterial, fungal or other infection may be treatable using a protein of the present invention, including infections by HIV, hepatitis viruses, herpesviruses, mycobacteria, Leishmania spp., malaria spp. and various fingal infections such as candidiasis. Of course, in this regard, a protein of the present invention may also be useful where a boost to the immune system generally may be desirable, i.e., in the treatment of cancer. Autoimmune disorders which may be treated using a protein of the present invention include, for example, connective tissue disease, multiple sclerosis, systemic lupus erythematosus, rheumatoid arthritis, autoimmune pulmonary inflammation, Guillain-Barre syndrome, autoimmune thyroiditis, insulin dependent diabetes mellitis, myasthenia gravis, graft-versus-host disease and autoimmune inflammatory eye disease. Such a protein of the present invention may also to be useful in the treatment of allergic reactions and conditions, such as asthma (particularly allergic asthma) or other respiratory problems. Other conditions, in which immune suppression is desired (including, for example, organ transplantation), may also be treatable using a protein of the present invention.

The MU-1 DNA also maps to the chromosomal locus for Crohn's disease. As a result, proteins of the present invention may be used to treat Crohn's disease and other inflammatory bowel diseases.

Using the proteins of the invention it is possible to modulate immune responses, in a number of ways. Down regulation may be in the form of inhibiting or blocking an immune response already in progress or may involve preventing the induction of an immune response. The functions of activated T cells may be inhibited by suppressing T cell responses or by inducing specific tolerance in T cells, or both. Immunosuppression of T cell responses is generally an active, non-antigen-specific, process which requires continuous exposure of the T cells to the suppressive agent. Tolerance, which involves inducing non-responsiveness or anergy in T cells, is distinguishable from immunosuppression in that it is generally antigen-specific and persists after exposure to the tolerizing agent has ceased. Operationally, tolerance can be demonstrated by the lack of a T cell response upon reexposure to specific antigen in the absence of the tolerizing agent.

Down regulating or preventing one or more antigen functions (including without limitation B lymphocyte antigen functions (such as, for example, B7)), e.g., preventing high level lymphokine synthesis by activated T cells, will be useful in situations of tissue, skin and organ transplantation and in graft-versus-host disease (GVHD). For example, blockage of T cell function should result in reduced tissue destruction in tissue transplantation. Typically, in tissue transplants, rejection of the transplant is initiated through its recognition as foreign by T cells, followed by an immune reaction that destroys the transplant. The administration of a molecule which inhibits or blocks interaction of a B7 lymphocyte antigen with its natural ligand(s) on immune cells (such as a soluble, monomeric form of a peptide having B7-2 activity alone or in conjunction with a monomeric form of a peptide having an activity of another B lymphocyte antigen (e.g., B7-1, B7-3) or blocking antibody), prior to transplantation can lead to the binding of the molecule to the natural ligand(s) on the immune cells without transmitting the corresponding costimulatory signal. Blocking B lymphocyte antigen function in this matter prevents cytokine synthesis by immune cells, such as T cells, and thus acts as an immunosuppressant. Moreover, the lack of costimulation may also be sufficient to anergize the T cells, thereby inducing tolerance in a subject. Induction of long-term tolerance by B lymphocyte antigen-blocking reagents may avoid the necessity of repeated administration of these blocking reagents. To achieve sufficient immunosuppression or tolerance in a subject, it may also be necessary to block the function of a combination of B lymphocyte antigens. The efficacy of particular blocking reagents in preventing organ transplant rejection or GVHD can be assessed using animal models that are predictive of efficacy in humans. Examples of appropriate systems which can be used include allogeneic cardiac grafts in rats and xenogeneic pancreatic islet cell grafts in mice, both of which have been used to examine the immunosuppressive effects of CTLA4Ig fusion proteins in vivo as described in Lenschow et al., Science 257:789–792 (1992) and Turka et al., Proc. Natl. Acad. Sci U.S.A., 89:11102–11105 (1992). In addition, murine models of GVHD (see Paul ed., Fundamental Immunology, Raven Press, New York, 1989, pp. 846–847) can be used to determine the effect of blocking B lymphocyte antigen function in vivo on the development of that disease.

Blocking antigen function may also be therapeutically useful for treating autoimmune diseases. Many autoimmune disorders are the result of inappropriate activation of T cells that are reactive against self tissue and which promote the production of cytokines and autoantibodies involved in the pathology of the diseases. Preventing the activation of autoreactive T cells may reduce or eliminate disease symptoms. Administration of reagents which block costimulation of T cells by disrupting receptor:ligand interactions of B lymphocyte antigens can be used to inhibit T cell activation and prevent production of autoantibodies or T cell-derived cytokines which may be involved in the disease process. Additionally, blocking reagents may induce antigen-specific tolerance of autoreactive T cells which could lead to long-term relief from the disease. The efficacy of blocking reagents in preventing or alleviating autoimmune disorders can be determined using a number of well-characterized animal models of human autoimmune diseases. Examples include murine experimental autoimmune encephalitis, systemic lupus erythmatosis in MRL/1pr/1pr mice or NZB hybrid mice, murine autoimmune collagen arthritis, diabetes mellitus in NOD mice and BB rats, and murine experimental myasthenia gravis (see Paul ed., Fundamental Immunology, Raven Press, New York, 1989, pp. 840–856).

Upregulation of an antigen function (preferably a B lymphocyte antigen function), as a means of up regulating immune responses, may also be useful in therapy. Upregulation of immune responses may be in the form of enhancing an existing immune response or eliciting an initial immune response. For example, enhancing an immune response through stimulating B lymphocyte antigen function may be useful in cases of viral infection. In addition, systemic viral diseases such as influenza, the common cold, and encephalitis might be alleviated by the administration of stimulatory forms of B lymphocyte antigens systemically.

Alternatively, anti-viral immune responses may be enhanced in an infected patient by removing T cells from the patient, costimulating the T cells in vitro with viral antigen-pulsed APCs either expressing a peptide of the present invention or together with a stimulatory form of a soluble peptide of the present invention and reintroducing the in vitro activated T cells into the patient. Another method of enhancing anti-viral immune responses would be to isolate infected cells from a patient, transfect them with a nucleic acid encoding a protein of the present invention as described herein such that the cells express all or a portion of the protein on their surface, and reintroduce the transfected cells into the patient. The infected cells would now be capable of delivering a costimulatory signal to, and thereby activate, T cells in vivo.

In another application, up regulation or enhancement of antigen function (preferably B lymphocyte antigen function) may be useful in the induction of tumor immunity. Tumor cells (e.g., sarcoma, melanoma, lymphoma, leukemia, neuroblastoma, carcinoma) transfected with a nucleic acid encoding at least one peptide of the present invention can be administered to a subject to overcome tumor-specific tolerance in the subject. If desired, the tumor cell can be transfected to express a combination of peptides. For example, tumor cells obtained from a patient can be transfected ex vivo with an expression vector directing the expression of a peptide having B7-2-like activity alone, or in conjunction with a peptide having B7-1-like activity and/or B7-3-like activity. The transfected tumor cells are returned to the patient to result in expression of the peptides on the surface of the transfected cell. Alternatively, gene therapy techniques can be used to target a tumor cell for transfection in vivo.

The presence of the peptide of the present invention having the activity of a B lymphocyte antigen(s) on the surface of the tumor cell provides the necessary costimulation signal to T cells to induce a T cell mediated immune response against the transfected tumor cells. In addition, tumor cells which lack MHC class I or MHC class II molecules, or which fail to reexpress sufficient amounts of MHC class I or MHC class II molecules, can be transfected with nucleic acid encoding all or a portion of (e.g., a cytoplasmic-domain truncated portion) of an MHC class .alpha. a chain protein and $\beta_2$ microglobulin protein or an MHC class II α chain protein and an MHC class II β chain protein to thereby express MHC class I or MHC class II proteins on the cell surface. Expression of the appropriate class I or class II MHC in conjunction with a peptide having the activity of a B lymphocyte antigen (e.g., B7-1, B7-2, B7-3) induces a T cell mediated immune response against the transfected tumor cell. Optionally, a gene encoding an antisense construct which blocks expression of an MHC class II associated protein, such as the invariant chain, can also be cotransfected with a DNA encoding a peptide having the activity of a B lymphocyte antigen to promote presentation of tumor associated antigens and induce tumor specific immunity. Thus, the induction of a T cell mediated immune response in a human subject may be sufficient to overcome tumor-specific tolerance in the subject.

The activity of a protein of the invention may, among other means, be measured by the following methods:

Suitable assays for thymocyte or splenocyte cytotoxicity include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Herrmann et al., Proc. Natl. Acad. Sci. U.S.A. 78:2488–2492, 1981; Herrmann et al., J. Immunol. 128: 1968–1974, 1982; Handa et al., J. Immunol. 135:1564–1572, 1985; Takai et al., J. Immunol. 137:3494–3500, 1986; Takai et al., J. Immunol. 140:508–512, 1988; Herrmann et al., Proc. Natl. Acad. Sci. U.S.A. 78:2488–2492, 1981; Herrmann et al., J. Immunol. 128:1968–1974, 1982; Handa et al., J. Immunol. 135:1564–1572, 1985; Takai et al., J. Immunol. 137:3494–3500, 1986; Bowmanet al., J. Virology 61:1992–1998; Takai et al., J. Immunol. 140:508–512, 1988; Bertagnolli et al., Cellular Immunology 133:327–341, 1991; Brown et al., J. Immunol. 153:3079–3092, 1994.

Assays for T-cell-dependent immunoglobulin responses and isotype switching (which will identify, among others, proteins that modulate T-cell dependent antibody responses and that affect Th1/Th2 profiles) include, without limitation, those described in: Maliszewski, J. Immunol. 144:3028–3033, 1990; and Assays for B cell function: In vitro antibody production, Mond, J. J. and Brunswick, M. In Current Protocols in Immunology. J. E. e.a. Coligan eds. Vol 1 pp. 3.8.1–3.8.16, John Wiley and Sons, Toronto. 1994.

Mixed lymphocyte reaction (MLR) assays (which will identify, among others, proteins that generate predominantly Th1 and CTL responses) include, without limitation, those described in: Current Protocols in Immunology, Ed by J. E. Coligan, A. M. Kruisbeek, D. H. Margulies, E. M. Shevach, W Strober, Pub. Greene Publishing Associates and Wiley-Interscience (Chapter 3, In Vitro assays for Mouse Lymphocyte Function 3.1–3.19; Chapter 7, Immunologic studies in Humans); Takai et al., J. Immunol. 137:3494–3500, 1986; Takai et al., J. Immunol. 140:508–512, 1988; Bertagnolli et al., J. Immunol. 149:3778–3783, 1992.

Dendritic cell-dependent assays (which will identify, among others, proteins expressed by dendritic cells that activate naive T-cells) include, without limitation, those described in: Guery et al., J. Immunol. 134:536–544, 1995; Inaba et al., Journal of Experimental Medicine 173:549–559, 1991; Macatonia et al., Journal of Immunology 154:5071–5079, 1995; Porgador et al., Journal of Experimental Medicine 182:255–260, 1995; Nair et al., Journal of Virology 67:4062–4069, 1993; Huang et al., Science 264:961–965, 1994; Macatonia et al., Journal of Experimental Medicine 169:1255–1264, 1989; Bhardwaj et al., Journal of Clinical Investigation 94:797–807, 1994; and Inaba et al., Journal of Experimental Medicine 172:631–640, 1990.

Assays for lymphocyte survival/apoptosis (which will identify, among others, proteins that prevent apoptosis after superantigen induction and proteins that regulate lymphocyte homeostasis) include, without limitation, those described in: Darzynkiewicz et al., Cytometry 13:795–808, 1992; Gorczyca et al., Leukemia 7:659–670, 1993; Gorczyca et al., Cancer Research 53:1945–1951, 1993; Itoh et al., Cell 66:233–243, 1991; Zacharchuk, Journal of Immunology 145:4037–4045, 1990; Zamai et al., Cytometry 14:891–897, 1993; Gorczyca et al., International Journal of Oncology 1:639–648, 1992.

Assays for proteins that influence early steps of T-cell commitment and development include, without limitation, those described in: Antica et al., Blood 84:111–117, 1994; Fine et al., Cellular Immunology 155:111–122, 1994; Galy et al., Blood 85:2770–2778, 1995; Toki et al., Proc. Nat. Acad Sci. U.S.A. 88:7548–7551, 1991.

Amino acid sequences of IL-21 polypeptides are publicly known. For example, the nucleotide sequence and amino acid sequence of a human IL-21 is available at Genbank Acc. No. X_011082. The disclosed human IL-21 nucleotide sequence is presented below:

porting the growth and proliferation of myeloid cells such as granulocytes and monocytes/macrophages (i.e., traditional CSF activity) useful, for example, in conjunction with chemotherapy to prevent or treat consequent myelo-suppression; in supporting the growth and proliferation of megakaryocytes and consequently of platelets thereby allowing prevention or treatment of various platelet disorders such as thrombocytopenia, and generally for use in place of or complimentary to platelet transfusions; and/or in supporting the growth and proliferation of hematopoietic stem cells which are capable of maturing to any and all of the above-mentioned hematopoietic cells and therefore find therapeutic utility in various stem cell disorders (such as those usually treated with transplantation, including, without limitation, aplastic anemia and paroxysmal nocturnal hemoglobinuria), as well as in repopulating the stem cell compartment post irradiation/chemotherapy, either in-vivo or ex-vivo (i.e., in conjunction with bone marrow transplantation or with peripheral progenitor cell transplantation (homologous or heterologous)) as normal cells or genetically manipulated for gene therapy.

```
  1 gctgaagtga aaacgagacc aaggtctagc tctactgttg gtacttatga gatccagtcc    (SEQ ID NO:18)

61 tggcaacatg gagaggattg tcatctgtct gatggtcatc ttcttgggga cactggtcca 121 caaatcaagc tcccaaggtc aagatcgcca catgattaga atgcgtcaac ttatagatat 181 tgttgatcag ctgaaaaatt atgtgaatga cttggtccct gaatttctgc cagctccaga 241 agatgtagag acaaactgtg agtggtcagc tttttcctgc tttcagaagg cccaactaaa 301 gtcagcaaat acaggaaaca atgaaaggat aatcaatgta tcaattaaaa agctgaagag 361 gaaaccacct tccacaaatg cagggagaag acagaaacac agactaacat gcccttcatg 421 tgattcttat gagaaaaaac cacccaaaga attcctagaa agattcaaat cacttctcca 481 aaagatgatt catcagcatc tgtcctctag aacacacgga agtgaagatt cctgaggatc 541 taacttgcag ttggacacta tgttacatac tctaatatag tagtgaaagt catttctttg 601 tattccaagt ggaggag
```

The amino acid sequence of the disclosed human IL-21 polypeptide is presented below:

```
                                                  (SEQ ID NO:19)
MRSSPGNMERIVICLMVIFLGTLVHKSSSQGQDRHMIRMRQLIDIVDQLK

NYVNDLVPEFLPAPEDVETNCEWSAFSCFQKAQLKSANTGNNERIINVSI

KKLKRKPPSTNAGRRQKHRLTCPSCDSYEKKPPKEFLERFKSLLQKMIHQ

HLSSRTHGSEDS
```

Hematopoiesis Regulating Activity

A protein of the present invention is useful in regulation of hematopoiesis and, consequently, in the treatment of myeloid or lymphoid cell deficiencies. Even marginal biological activity in support of colony forming cells or of factor-dependent cell lines indicates involvement in regulating hematopoiesis, e.g. in supporting the growth and proliferation of erythroid progenitor cells alone or in combination with other cytokines, thereby indicating utility, for example, in treating various anemias or for use in conjunction with irradiation/chemotherapy to stimulate the production of erythroid precursors and/or erythroid cells; in sup- The activity of a protein of the invention may, among other means, be measured by the following methods:

Suitable assays for proliferation and differentiation of various hematopoietic lines are cited above.

Assays for embryonic stem cell differentiation (which will identify, among others, proteins that influence embryonic differentiation hematopoiesis) include, without limitation, those described in: Johansson et al. Cellular Biology 15:141–151, 1995; Keller et al., Molecular and Cellular Biology 13:473–486, 1993; McClanahan et al., Blood 81:2903–2915, 1993.

Assays for stem cell survival and differentiation (which will identify, among others, proteins that regulate lymphohematopoiesis) include, without limitation, those described in: Methylcellulose colony forming assays, Freshney, M.G. In Culture of Hematopoietic Cells. R. I. Freshney, et al. eds. Vol pp. 265–268, Wiley-Liss, Inc., New York, N.Y. 1994; Hirayama et al., Proc. Natl. Acad. Sci. U.S.A. 89:5907–5911, 1992; Primitive hematopoietic colony forming cells with high proliferative potential, McNiece, I. K. and Briddell, R. A. In Culture of Hematopoietic Cells. R. I. Freshney, et al. eds. Vol pp. 23–39, Wiley-Liss, Inc., New York, N.Y. 1994; Neben et al., Experimental Hematology 22:353–359, 1994; Cobblestone area forming cell assay, Ploemacher, R. E. In Culture of Hematopoietic Cells. R. I. Freshney, et al. eds. Vol pp. 1–21, Wiley-Liss, Inc., New York, N.Y. 1994; Long term bone marrow cultures in the presence of stromal cells, Spooncer, E., Dexter, M. and Allen, T. In Culture of Hematopoietic Cells. R. I. Freshney, et al. eds. Vol pp. 163–179, Wiley-Liss, Inc., New York, N.Y. 1994; Long term culture initiating cell assay, Sutherland, H. J. In Culture of Hematopoietic Cells. R. I. Freshney, et al. eds. Vol pp. 139–162, Wiley-Liss, Inc., New York, N.Y. 1994.

Research Uses and Utilities

Polynucleotides provided by the present invention can be used by the research community for various purposes. The polynucleotides can be used to express recombinant protein for analysis, characterization or therapeutic use; as markers for tissues in which the corresponding protein is preferentially expressed (either constitutively or at a particular stage of tissue differentiation or development or in disease states); as molecular weight markers on Southern gels; as chromosome markers or tags (when labeled) to identify chromosomes or to map related gene positions; to compare with endogenous DNA sequences in patients to identify potential genetic disorders; as probes to hybridize and thus discover novel, related DNA sequences; as a source of information to derive PCR primers for genetic fingerprinting; as a probe to "subtract-out" known sequences in the process of discovering other novel polynucleotides; for selecting and making oligomers for attachment to a "gene chip" or other support, including for examination of expression patterns; to raise anti-protein antibodies using DNA immunization techniques; and as an antigen to raise anti-DNA antibodies or elicit another immune response. Where the polynucleotide encodes a protein which binds or potentially binds to another protein (such as, for example, in a receptor-ligand interaction), the polynucleotide can also be used in interaction trap assays (such as, for example, that described in Gyuris et al., Cell 75:791–803 (1993)) to identify polynucleotides encoding the other protein with which binding occurs or to identify inhibitors of the binding interaction.

The proteins provided by the present invention can similarly be used in assay to determine biological activity, including in a panel of multiple proteins for high-throughput screening; to raise antibodies or to elicit another immune response; as a reagent (including the labeled reagent) in assays designed to quantitatively determine levels of the protein (or its receptor) in biological fluids; as markers for tissues in which the corresponding protein is preferentially expressed (either constitutively or at a particular stage of tissue differentiation or development or in a disease state); and, of course, to isolate correlative receptors or ligands. Where the protein binds or potentially binds to another protein (such as, for example, in a receptor-ligand interaction), the protein can be used to identify the other protein with which binding occurs or to identify inhibitors of the binding interaction. Proteins involved in these binding interactions can also be used to screen for peptide or small molecule inhibitors or agonists of the binding interaction.

Any or all of these research utilities are capable of being developed into reagent grade or kit format for commercialization as research products.

Methods for performing the uses listed above are well known to those skilled in the art. References disclosing such methods include without limitation "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

Nutritional Uses

Polynucleotides and proteins of the present invention can also be used as nutritional sources or supplements. Such uses include without limitation use as a protein or amino acid supplement, use as a carbon source, use as a nitrogen source and use as a source of carbohydrate. In such cases the protein or polynucleotide of the invention can be added to the feed of a particular organism or can be administered as a separate solid or liquid preparation, such as in the form of powder, pills, solutions, suspensions or capsules. In the case of microorganisms, the protein or polynucleotide of the invention can be added to the medium in or on which the microorganism is cultured.

MU-1 proteins of the invention may also be used to immunize animals to obtain polyclonal and monoclonal antibodies which specifically react with the MU-1 protein and which may inhibit binding of ligands to the receptor. Such antibodies may be obtained using the entire MU-1 as an immunogen, or by using fragments of MU-1. Smaller fragments of the MU-1 may also be used to immunize animals. The peptide immunogens additionally may contain a cysteine residue at the carboxyl terminus, and are conjugated to a hapten such as keyhole limpet hemocyanin (KLH). Additional peptide immunogens may be generated by replacing tyrosine residues with sulfated tyrosine residues. Methods for synthesizing such peptides are known in the art, for example, as in R. P. Merrifield, J.Amer.Chem.Soc. 85, 2149–2154 (1963); J. L. Krstenansky, et al., FEBS Lett. 211, 10 (1987).

Neutralizing or non-neutralizing antibodies (preferably monoclonal antibodies) binding to MU-1 protein may also be useful therapeutics for certain tumors and also in the treatment of conditions described above. These neutralizing monoclonal antibodies may be capable of blocking ligand binding to the MU-1 receptor chain.

The present invention further provides for compositions comprising an antibody which specifically reacts with a protein of the present invention.

The invention also provides a method for inhibiting T-cell proliferation by contacting a population of T cells with a MU-1 polypeptide antagonist in an amount sufficient to inhibit proliferation of the T-cell population. Also provided are methods for increasing T-cell proliferation by contacting a population of T cells with an agent that increases levels of IL-21, the ligand for the MU-1 polypeptide, in a population of T cells. The methods are based in part on the discovery that IL-21 enhances anti-CD3-induced proliferation of thymocytes, lymph node T cells, and purified $CD4^+$ or $CD8^+$ cells. The inventors have also determined that IL-21 augments proliferation of T cells in response to alloantigens. Priming of $CD8^+$ T cells in the presence of IL-21 generates potent effector cells with enhanced lytic activity and increased their ability to produce IFNγ. Il-21 also has effects on memory T cells and antigen presenting cells (APCs). IL-21 has also been found to be produced by activated $CD4^+$ cells. These discoveries provide the basis for methods of inhibiting T cell proliferation by contacting a T cell population with an antagonist of MU-1, e.g., a polypeptide antagonist of MU-1. Antagonists (such as polypeptide antagonists) of IL-21 can also be administered to subjects for which inhibition of an immune response is desired. These conditions include, e.g., autoimmune disorders, or organ transplantation. Conversely, IL-21, or an agent that increases IL-21 levels, can be added to T cells for situations in which proliferation of T cells is desired, or enhancement of an immune response (particularly a T cell-mediated immune response) is desired. Enhancement of immune responses are desirable for subjects having cancer or an infectious disease.

The invention will be further illustrated in the following non-limiting examples.

EXAMPLE 1

Isolation and Characterization of Murine MU-1 cDNAs

A partial fragment of the murine homolog of the Mu-1 receptor was isolated by PCR using oligonucleotides derived from the human sequences. cDNA was prepared from RNA isolated from 17 day old murine thymus and from the murine 2D6 T cell line. A DNA fragment of approximately 300 nucleotides was amplified from the cDNA by PCR with the following oligonucleotides, corresponding to regions 584–603 and 876–896, respectively, of the human cDNA sequence in FIG. 1A and FIG. 1B (corresponding to SEQ ID NO: 1):

```
AGCATCAAG CCGGCTCCCCC (5p) (SEQ ID NO:11)

CTCCATTCAC TCCAGGTCCC (3p) (SEQ ID NO:12)
```

Amplification was carried out using Taq polymerase in 1× Taq buffer containing 1.5 mM of magnesium chloride for 30 cycles at 94° C. for one minute, 50° C. for 1 minute, and 72 ° C. for one minute. The DNA sequence of this fragment was determined, and two oligonucleotides were derived from an internal portion of this fragment with the following sequences:

```
TTGAACGTGACTGRGGCCTT (5P) (SEQ ID NO:13)

TGAATGAAGTGCCTGGCTGA (3P) (SEQ ID NO:14)
```

The oligonucleotides were used to amplify an internal 262 nucleotide fragment of the original PCR product (corresponding to nucleotides 781–1043 of the murine cDNA sequence of FIG. 1A and FIG. 1B, and SEQ ID NO:9) to use as a hybridization probe to screen a cDNA library isolated from the 2D6T T cell line. Filters were hybridized at 65° C. using standard 5×SSC hybridization conditions and washed into SSC at 65 ° C. Twenty clones were hybridizes to the probe in a screen of 426,000 clones. DNA sequence was determined from two independent clones. Full length sequence of clone #6 confirmed that it was the full-length murine homolog of human MU-1 (SEQ ID NO:9).

The full-length nucleotide sequence of murine MU-1 is shown in FIG. 1A and FIG. 1B (corresponding to SEQ ID NO:9). The nucleotide sequence has a predicted leader sequence at nucleotides 407–464, coding sequence at 407–1993, and a termination codon at nucleotides 1994–1997. Nucleotides 1–406 correspond to the 5' untranslated region and nucleotides 1998–2868 correspond to the 3' untranslated region.

The predicted protein sequence of murine MU-1 is shown in FIG. 2 (corresponding to SEQ ID NO:10). This murine MU-1 protein contains a predicted leader sequence determined by SPScan (score=10.1)(corresponding to amino acids 1–19 of SEQ ID NO:10), and a predicted transmembrane domain (corresponding to amino acids 237–253 of SQ ID NO:10). Predicted signaling motifs include the following regions: Box 1: amino acids 265–274 of SEQ ID NO:10, Box 2: amino acids 310–324 of SEQ ID NO:10, six tyrosine residues at positions 281, 319, 361, 297, and 510 of SEQ ID NO:10. Potential STAT docking sites include: STAT5, EDDGYPA (SEQ ID NO:20); STAT3, YLQR.

The oligonucleotides were used to amplify an internal 262 nucleotide fragment of the original PCR product (corresponding to nucleotides 781–1043 in of the murine cDNA sequence of FIG. 1A and FIG. 1B, and SEQ ID NO:9) to use as a hybridization probe to screen a cDNA library isolated from the 2D6 T cell line. Filters were hybridized at 65° C. using standard 5×SSC hybridization conditions and washed into SSC at 65° C. Twenty clones were isolated that hybridized to the probe in a screen of 426,000 clones. DNA sequence was determined from two independent clones. Full length sequence of clone #6 confirmed that it was the full-length murine homolog of human MU-1 (SEQ ID NO:9).

The full-length nucleotide sequence of murine MU-1 is shown in FIG. 1A and FIG. 1B (corresponding to SEQ ID NO:9). The nucleotide sequence has a predicted leader sequence at nucleotides 407–464, coding sequence at nucleotides 407–1993, termination codon at nucleotides 1994–1997. Nucleotides 1–406 correspond to the 5' untranslated region and nucleotides 1998–2628 correspond to the 3' untranslated region.

The predicted protein sequence of murine MU-1 is shown in FIG. 2 (corresponding to SEQ ID NO:10). This murine MU-1 protein contains a predicted leader sequence determined by SPScan (score=10.1) (corresponding to amino acids 1–19 of SEQ ID NO:10), and a predicted transmembrane domain (corresponding to amino acids 237–253 of SEQ ID NO:10). Predicted signaling motifs include the following regions: Box 1: amino acids 265–274 of SEQ ID NO:10, Box 2: amino acids 310–324 of SEQ ID NO:10, six tyrosine residues at positions 281, 319, 361, 368, 397, and 510 of SEQ ID NO:10. Potential STAT docking sites include: STAT5: EDDGYPA (SEQ ID NO:20), STAT 3:YLQR.

EXAMPLE 2

Comparison of Human and Murine MU-1

The GAP algorithm was used to compare the human and murine MU-1 amino acids. A comparison of the murine and human predicted protein sequences is shown in FIG. 4. The amino acids were 65.267% identical using the GAP algorithm. The alignment was generated by BLOSUM62 amino acid substitution matrix (Henikoff, S. and Henikoff, J. G. (1992)). Amino acid substitution matrices from protein blocks (Proc. Natl. Acad. Sci. USA 89: 10915–10919). Gap parameters=Gap Weight: 8, Average Match=2.9 12, Length Weight=2, Average Mismatch=–2.003. Percent Similarity=69.466.

A comparison of the human and murine cDNA nucleotide sequences is shown in FIGS. 3A–D. The DNA sequences are 66.116% identical when aligned using the GAP algorithm. Gap Parameters: Gap Weight=50, Average Match 10.000, Length Weight=3, Average Mismatch=0.000. Percent Similarity=66.198.

Both human and mouse MU-1 proteins are members of the Type 1 cytokine receptor superfamily. Evaluation of the sequence of both murine and human MU-1 reveals the presence of potential Box-i and Box-2 signaling motifs. Six tyrosine residues are present in the cytoplasmic domain, and could also be important in signaling functions of MU-1. Comparison of the sequences of MU-1 with other members of the family suggested the presence of potential docking sites for STAT 5 and STAT 3.

EXAMPLE 3

Determination of STAT signaling pathways used by Human MU-1

BAF-3 cells were engineered to express a chimeric cytokine receptor consisting of the extracellular domain of the human EPO receptor and the intracellular domain of the MU-1 receptor. BAF-3 cells that expressed huEPORJMU-1(cyto) chimeric receptors proliferated in response to human soluble EPO. These cells were analyzed to determine which STAT molecules were phosphorylated in response to EPO signaling. Briefly, control unmodified parental BAF-3 cells and EPOR/MU chimeric BAF-3 cells were rested from IL-3 containing growth medium, and restimulated with either IL-3 or EPO for 0, 15, 30 and 60 minutes. The cells were pelleted and resuspended in ice cold lysis buffer containing orthovanadate, to preserve phosphorylated tyrosines. Equal amounts of cell lysate were electrophoresed by SDS-PAGE and blotted onto nitrocellulose membranes for western analysis. Duplicate blots were stained for phosphorylated and nonphosphoraled forms of STAT 1, 3, 5, and 6 by using antibodies specific for each form of the STAT molecule. HELA cells, non-activated and activated with alpha-interferon were used as positive controls.

These results indicated that under these specific conditions, signaling through MU-1 results in the phosphorylation of STAT 5 at all time-points tested (1=0, T=15', T=30', 1=60'). Treatment of controls or the chimeric BAF-3 cells with IL-3 resulted in phosphorylation of STAT 3, but not STAT 1 or 5.

EXAMPLE 4

Tissue Expression of Murine and Human MU-1

Northern Analysis

Northern blots of polyA+RNA from various tissues (Clonetech, Palo Alto, Calif.) were performed as recommended by the manufacturer. For the murine blots, a 262 nucleotide fragment corresponding to nucleotides 781–1043 of FIG. 1A and FIG. 1B and SEQ ID NO:9 was used for hybridization.

A single transcript of murine MU-1 was detected in adult murine spleen, lung, and heart tissues. The larger transcript observed in human tissues was not observed in mouse tissues.

Two transcripts of human MU-1 were detected in adult human lymphoid tissues, PBLs, thymus, spleen and lymph node, and in fetal lung.

In Situ Hybridization

In situ hybridization studies were performed by Phylogency Inc. of Columbus, Ohio (according to the method of Lyons et al., 1990, J. Cell. Biol: 111:2427–2436.) Briefly, serial 5–7 micron paraffin sections were deparaffinized, fixed, digested with proteinase K, treated with tri-ethanolamine and dehydrated. cRNAs were prepared from linearized cDNA templates to generate antisense and sense probes. The cRNA transcripts were synthesized according to manufacturer's conditions (Ambion) and labeled with 35S-UTP. Sections were hybridized overnight, stringently washed and treated with RNAase A and dipped in nuclear track emulsion and exposed for 2–3 weeks. Control sections were hybridized with sense probes to indicate the background level of the procedure. The murine probe consisted of a n 186 bp fragment corresponding to nucleotides 860–1064 (SEQ ID NO:9). The human probe was a 23 bp PCR product generated from human MU-1 DNA.

Murine MU-1 expression was observed in the lymph nodes of the adult small intestine at germinal centers and muscular is external. Specialized lymph nodes and Peyers patches also exhibited murine MU-1 expression.

Human MU-1 expression was detected at germinal centers of the lymph nodules in the cortex. The medulla, which contains macrophages, was negative for human MU-1. In human spleen, human MU-1 expression was detected in the regions of white pulp but not red pulp.

EXAMPLE 5

Expression of Human MU-1 in Cells and Cell Lines

RNAse protection analysis was performed on resting and activated human T cells and the B cell lines, Raji and RPMI 8866, and the I cell line Jurkat. Human T cells were activated with anti-CD3 and anti-CD28. The cell lines were activated by Phorbol ester and ionomycin. MU-1 riboprobe-producing plasmid was constructed by inserting a 23 bp PCR product (PCR was performed by using 5' primer CACAAAGCTTCAGTATGAGCTGCAGTA-CAGGAACCGGGGA (SEQ ID NO: 15) and 3' primer CACAGGATCCCTTTAACTCCTCT-GACTGGGTCTGAAAGAT (SEQ ID NO:16)) into the BamH I and HindIll sites of pGEM3zf(-) (Promega, Madison, Wis.) vector. To make the riboprobe, the riboprobe-producing plasmid was linearized with HindIII. The resulting DNA was phenol/chloroform extracted and precipitated with ethanol. T7 RNA polymerase was used to make the riboprobe according to the protocol suggested by the vendor (PharMingen, San Diego, Calif.). The RNAse protection assay was performed by using PharMingen's RiboQuant Multi-Probe Ribonuclease Protection Assay system. 2.Oug of total RNA were included in each RPA reaction, after RNAse digestion, the protected riboprobes were run on a QuickPoint rapid nucleic acid separation system (Novex, San Diego, Calif.). Gels were dried and exposed according to the suggestion of the vendor.

Human MU-1 RNA is upregulated in anti-CD3 +anti-CD28 stimulated human purified CD3+ cells when compared with unstimulated populations. MU-1 is also upregulated upon restimulation in Th1 and Th2-skewed T cell populations. The B cell lines, RPM! 8866 and Raji, constitutively express MU-1 while the Jurkat T cell line does not.

Example 6

Binding of Human MU-1 to Known Cytokines

Both human and murine Ig fusion proteins were constructed and immobilized on Biacore chips in an effort to identify the ligand for MU-1. A variety of cell culture conditioned media as well as a panel of known cytokines were evaluated for binding to MU-1. Some cytokines were also tested in combination with other receptor chains in the family to consider the possibility that MU-1 may require a second receptor chain for ligand binding. The following cytokines were tested and found to be negative for MU-1 binding: mIL-2, hIL-2, hIL-i5, mIL-7, TSLP, TSLP+IL7, TSLP+IL7R, TSLP+IL7g, TSLP+IL-2, TSLP +1L2 +IL2Rbeta, IL2Rbeta, 1L2Rgamma, IL7R, 1L2+2Rbeta, 1L2+2Rgamma, IL1 5+IL2Rbeta, 1L15+2Rgamma, 1L7+ 2Rgamma, IL2+IL7R, IL1 5+IL7R, IL7+IL7R. Known receptors have been immobilized as well and tested for MUFc binding with negative results. IL-IS will bind to IL2Rb but not IL2Rg or MUFc.

Additional embodiments are within the claims.

What is claimed is:

1. A method of suppressing an immune response in a subject, comprising administering to the subject a therapeutically effective amount of a soluble polypeptide, wherein said polypeptide is encoded by a polynucleotide that hybridizes under stringent conditions of 0.1×SSC, 65° C. to the complement of the nucleotide sequence set forth in SEQ ID NO:1, and wherein said polypeptide binds IL-21.

2. The method of claim 1, wherein said subject has an autoimmune disorder.

3. The method of claim 2, wherein said autoimmune disorder is selected from the group consisting of rheumatoid arthritis, and systemic lupus erythematosus.

4. The method of claim 3, wherein said autoimmune disorder is rheumatoid arthritis.

5. The method of claim 3, wherein said autoimmune disorder is systemic lupus erythematosus.

6. The method of claim 1, wherein said subject has Crohn's disease or IBD.

7. The method of claim 1, wherein said immune response is to a transplanted organ.

8. The method of claim 1, wherein said soluble polypeptide comprises from about amino acid 22 to about amino acid 236 of SEQ ID NO:2.

9. The method of claim 1, wherein said soluble polypeptide comprises from about amino acid 1 to about amino acid 236 of SEQ ID NO:2.

10. The method of claim 1, 8, or 9, wherein said soluble polypeptide is a fusion protein.

11. The method of claim 10, wherein said fusion protein comprises an antibody fragment.

12. The method of claim 11, wherein said antibody fragment is an Fc fragment.

13. The method of claim 1, wherein said subject is a human.

14. The method of claim 12, wherein said subject has rheumatoid arthritis.

15. A method of suppressing an immune response in a subject, comprising administering to the subject a therapeutically effective amount of an antagonistic antibody that binds specifically to the amino acid sequence set forth in SEQ ID NO:2.

16. The method of claim 15, wherein said subject has an autoimmune disorder.

17. The method of claim 16, wherein said autoimmune disorder is selected from the group consisting of rheumatoid arthritis, and systemic lupus erythematosus.

18. The method of claim 16, wherein said autoimmune disorder is rheumatoid arthritis.

19. The method of claim 16, wherein said autoimmune disorder is systemic lupus erythematosus.

20. The method of claim 15, wherein said subject has Crohn's disease or IBD.

21. The method of claim 15, wherein said immune response is to a transplanted organ.

22. The method of claim 15, wherein said antibody is a neutralizing antibody.

23. The method of claim 15, wherein said antibody is a monoclonal antibody.

24. The method of claim 15, wherein said subject is a human.

25. A method of suppressing an immune response in a subject, comprising administering to the subject a therapeutically effective amount of a soluble polypeptide, wherein said polypeptide comprises at least 90 contiguous amino acid residues of the amino acid of SEQ ID NO:2.

26. The method of claim 25, wherein said polypeptide comprises at least 100 contiguous amino acid residues of the amino acid of SEQ ID NO:2.

27. A method of suppressing an immune response in a subject, comprising administering to the subject a therapeutically effective amount of a soluble polypeptide, wherein said polypeptide is a fusion polypeptide comprising a soluble fragment of a MU-1 protein, wherein said soluble fragment comprises at least 90 contiguous amino acid residues of the amino acid sequence of SEQ ID NO:2 linked to a heterologous polypeptide.

28. The method of claim 27, wherein said soluble fragment comprises at least 100 contiguous amino acid residues of the amino acid sequence of SEQ ID NO:2 linked to a heterologous polypeptide.

29. The method of claim 28, wherein said heterologous polypeptide is an antibody fragment.

30. The method of claim 29, wherein, said antibody fragment is an Fc fragment.

31. The method of claim 27, wherein said subject has an autoimmune disorder.

32. The method of claim 31, wherein said autoimmune disorder is selected from the group consisting of rheumatoid arthritis, and systemic lupus erythematosus.

33. The method of claim 31, wherein said autoimmune disorder is rheumatoid arthritis.

34. The method of claim 31, wherein said autoimmune disorder is systemic lupus erythematosus.

35. The method of claim 27, wherein said subject has Crohn's disease or IBD.

36. The method of claim 27, wherein said immune response is to a transplanted organ.

37. The method of any of claims 1, 15, 25, or 27, further comprising administering to the subject a therapeutic agent selected from the group consisting of a cytokine inhibitor, a growth factor inhibitor, an immunosuppressant, an anti-inflammatory agent, a metabolic inhibitor, an enzyme inhibitor, a cytotoxic agent, and a cytostatic agent.

38. The method of claim 37, wherein the therapeutic agent is selected from the group consisting of a TNF antagonist, an IL-12 antagonist, an IL-15 antagonist, an IL-17 antagonist, an IL-18 antagonist, an IL-22 antagonist, a T cell-depleting agent, a B cell-depleting agent, methotrexate, leflunomide, rapamycin or an analog thereof, FK506, cyclosporine, a Cox-2 inhibitor, a cPLA2 inhibitor, an NSAID, and a p38 inhibitor.

* * * * *

UNITED STATES PATENT AND TRADEMARK OFFICE
CERTIFICATE OF CORRECTION

PATENT NO. : 7,189,400 B2
APPLICATION NO. : 09/972218
DATED : March 13, 2007
INVENTOR(S) : Laura Carter et al.

It is certified that error appears in the above-identified patent and that said Letters Patent is hereby corrected as shown below:

ON COVER PAGE AT ITEM (63) RELATED U.S. APPLICATION DATA

"application No. 09/950,766," should read --application No, 09/560,766--.

COLUMN 1

Line 23, "been identified" should read --have been identified--; and
Line 25, "exhibits" should read --exhibit--.

COLUMN 3

Line 36, "$CD8_+$ cells, $CD4_+$ cells," should read --$CP8^+$ cells, $CD4^+$ cells,--;
Line 43, "be" (second occurrence) should be deleted; and
Line 52, "$CD8_+$ cells, $CD4_+$ cells," should read --$CD8^+$ cells, $CD4^+$ cells,--.

COLUMN 4

Line 35, "FIGS. 3A-D" should read --FIGS. 3A-3D--; and
Line 67, "or5." should read --or 5.--.

COLUMN 5

Line 10, close up right margin.

COLUMN 6

Line 12 "fusions" should read --fusion--;
Line 21, "is" should be deleted; and
Line 53, "mu-1" should read --Mu-1--.

COLUMN 7

Line 3, "comprise" should read --comprises--;
Line 18, "tide" should read --tides--; and
Line 19, "5,428,130;5,514,582;" should read --5,428,130; 5,514,582;--; and
Line 30, "that" should read --than--.

COLUMN 10

Line 37, "which" should be deleted.

UNITED STATES PATENT AND TRADEMARK OFFICE
CERTIFICATE OF CORRECTION

PATENT NO. : 7,189,400 B2
APPLICATION NO. : 09/972218
DATED : March 13, 2007
INVENTOR(S) : Laura Carter et al.

It is certified that error appears in the above-identified patent and that said Letters Patent is hereby corrected as shown below:

COLUMN 13

Line 30, "causes" should read --caused--;
Line 34, "fingal" should read --fungal--; and
Line 46, "to" should be deleted.

COLUMN 18

Line 9, "complimentary" should read --complementary--.

COLUMN 20

Line 57, "I1-21" should read --IL-21--.

COLUMN 21

Line 48, "hybridizes" should read --hybridized--; and
Line 67, "SQ" should read --SEQ--.

COLUMN 22

Line 57, "FIGS. 3A-D." should read --FIGS. 3A-3D.--.

COLUMN 23

Line 27, "nonphosphoraled" should read --nonphosphorylated--.

COLUMN 24

Line 4, "a n" should read --a--;
Line 41, "2.0ug" should read --2.0 μg--; and
Line 54, "Example 6" should read --¶ EXAMPLE 6--.

UNITED STATES PATENT AND TRADEMARK OFFICE
CERTIFICATE OF CORRECTION

| | |
|---|---|
| PATENT NO. | : 7,189,400 B2 |
| APPLICATION NO. | : 09/972218 |
| DATED | : March 13, 2007 |
| INVENTOR(S) | : Laura Carter et al. |

It is certified that error appears in the above-identified patent and that said Letters Patent is hereby corrected as shown below:

<u>COLUMN 48</u>

Line 13, "wherein," should read --wherein--.

Signed and Sealed this

Eleventh Day of September, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,189,400 B2 | Page 1 of 1 |
| APPLICATION NO. | : 09/972218 | |
| DATED | : March 13, 2007 | |
| INVENTOR(S) | : Laura Carter et al. | |

It is certified that error appears in the above-identified patent and that said Letters Patent is hereby corrected as shown below:

Title Page Item (63) Related U.S. Application Data

"Continuation-in-part of application No. 09/569,384, filed on May 11, 2000, and a continuation-in-part of application No. 09/560,766, filed on Apr. 28, 2000, now abandoned, and a continuation-in-part of application No. 09/040,005, filed on Mar. 17, 1998, now Pat. No. 6,057,128."

should read --Continuation-in-part of application No. 09/569,384, filed on May 11, 2000, which is a continuation-in-part of application No. 09/560,766, filed on Apr. 28, 2000, now abandoned, which is a continuation of application No. 09/040,005, filed on Mar. 17, 1998, now Pat. No. 6,057,128.--

COLUMN 1:

Line 7, "May 11, 2000;" should read --May 11, 2000, which is a continuation-in-part of--

COLUMN 1:

Line 8, "abandoned; and" should read --abandoned, which is a continuation of--

Signed and Sealed this
Thirteenth Day of December, 2011

David J. Kappos
*Director of the United States Patent and Trademark Office*